US008507220B2

(12) United States Patent
Mori et al.

(10) Patent No.: US 8,507,220 B2
(45) Date of Patent: Aug. 13, 2013

(54) TOBACCO BY2 CELLS CONTAINING A TOMATO MOSAIC VIRUS VECTOR FOR PROTEIN PRODUCTION

(75) Inventors: Masashi Mori, Ishikawa (JP); Koji Dohi, Hakusan (JP); Masayuki Ishikawa, Tsukuba (JP); Tetsuo Meshi, Tsukuba (JP); Masaki Nishikiori, Mobara (JP); Atsushi Tamai, Abiko (JP)

(73) Assignee: Japan Science and Technology Agency, Kawaguchi-Shi, Saitama (JP)

( * ) Notice: Subject to any disclaimer, the term of this patent is extended or adjusted under 35 U.S.C. 154(b) by 1580 days.

(21) Appl. No.: 10/574,112

(22) PCT Filed: Oct. 1, 2004

(86) PCT No.: PCT/JP2004/014487
§ 371 (c)(1),
(2), (4) Date: Mar. 31, 2006

(87) PCT Pub. No.: WO2005/033306
PCT Pub. Date: Apr. 14, 2005

(65) Prior Publication Data
US 2009/0017490 A1 Jan. 15, 2009

(30) Foreign Application Priority Data

Oct. 1, 2003 (JP) ................................. 2003-343747
Oct. 8, 2003 (JP) ................................. 2003-350091
Mar. 1, 2004 (JP) ................................. 2004-056912

(51) Int. Cl.
*C12P 21/02* (2006.01)
*C12N 15/04* (2006.01)
*C12N 15/83* (2006.01)

(52) U.S. Cl.
USPC ........... 435/69.1; 435/414; 435/469; 435/470

(58) Field of Classification Search
None
See application file for complete search history.

(56) References Cited

U.S. PATENT DOCUMENTS

| | | | |
|---|---|---|---|
| 6,452,068 B1 * | 9/2002 | Zuo et al. | 800/278 |
| 2002/0061309 A1 * | 5/2002 | Garger et al. | 424/184.1 |
| 2003/0074677 A1 * | 4/2003 | Rasochova et al. | 800/8 |

FOREIGN PATENT DOCUMENTS

| | | |
|---|---|---|
| CA | 2 329 509 A1 | 12/1999 |
| CA | 2 388 755 A1 | 5/2001 |
| WO | WO 01/38512 A2 | 5/2001 |
| WO | WO 02/057301 A2 | 7/2002 |

OTHER PUBLICATIONS

David et al. Characterization of a Tobacco Bright Yellow 2 cell line expressing the tetracycline repressor at a high level for strict regulation of transgene expression. Plant Physiology, vol. 125, pp. 1548-1553, Apr. 2001.*
Martinez et al. Ecdysone agonist inducible transcription in transgenic tobacco plants. The Plant Journal, vol. 19, No. 1, pp. 97-106, 1999.*
Weber et al. A cDNA clone of tomato mosaic virus is infectious in plants. Journal of Virology, vol. 66, No. 6, pp. 3909-3912, Jun. 1992.*
Japanese Office Action dated May 12, 2009 in corresponding Japanese Application No. 2003-350091, with English translation.
Japanese Office Action dated May 19, 2009 in corresponding Japanese Application No. 2004-56912, with full English translation.
Wang et al., "Chemically regulated expression systems and their applications in transgenic plants", *Transgenic Research* 12: 529-540 (2003).
Shinmyo et al., "Molecular Improvement Technique for Plant Metabolic Engineering", Handbook of Plant Metabolic Engineering, NTS Inc. (Jun. 25, 2002), with English translation, pp. 244-251.
European Search Report for corresponding patent application 04791954.2-2401, Jan. 9, 2006.
Canadian Office Action corresponding to Canadian Application No. 2,540,668 dated Jan. 19, 2009.
Masayuki Mori et al., "2. Shokubutsu Bunshi Iden Kenkyushitsu (1) Shokubutsu Virus o Mochiita Kokoritsu Tanpakushitsu Goseikei no Kaihatsu 1. Estrogen Seigyokei o Mochiita Yudo mRNA Zofukukei no Kochiku, 2. Tomato Mosaic Virus Vector no Shokubutsu ni Okeru Steroid Hormone ni your Yudo Hatsugen", Ishikawa-Ken Nogyo Tanki Daigaku Fuzoku Nogyo SHigen Kenkyu sho Heisei 13 nendo Nenpo (2002), No. 10, pp. 13 to 16.
Masayuki Mori et al., "2. Shokubutsu Bunshi Iden Kenkyushitsu (1) Kokoritsu mRNA Yudo Zofukukei no Kochiku", Ishikawa-ken Nogyo Tanki Daigaku Fuzoku Nogyo Shigen Kenkyusho Heisei 12 Nendo Nenpo (2001), No. 9, pp. 16 to 18.
Mori et al, Inducible high-level mRNA amplification system by viral replicase in transgenic plants., Plant J. (2001), vol. 27, No. 1, pp. 79 to 86.
Masayuki Mori et al., "2. Shokubutsu Bunshi Iden Kenkyushitsu (1) Tabacco Mosaic Virus no Zoshoku Kiko no Kaimei", Ishikawa-Ken Nogyo Tanki Daigaku Fuzoku Nogyo Shigen Kenkyu sho Heisei 14 Nendo Nenpo (Dec. 26, 2003), No. 11, pp. 13 to 15.
International Search Report, International Preliminary Examination Report for PCT/JP2004/14487.
Annual Report, No. 9, 2000, Laboratory of Plant Molecular Genetics, Research Institute of Agricultural Resources, Ishikawa Agricultural College, Oct. 25, 2001, pp. 16-18.
Annual Report, No. 10, 2001, Laboratory of Plant Molecular genetics, Research Institute of Agricultural Resources, Ishikawa Agricultural College, Sep. 25, 2002, pp. 13-16.

(Continued)

*Primary Examiner* — Jennifer Dunston
(74) *Attorney, Agent, or Firm* — Harness, Dickey & Pierce, P.L.C.

(57) ABSTRACT

An expression vector is constructed by transferring recombinant tomato mosaic virus (ToMV) cDNA, in which a coat protein gene of ToMV having a suppressor against a virus resistant reaction has been substituted by a GFP gene, into the downstream of a promoter capable of inducing steroid hormone-dependent transcription. In a transformed tobacco BY-2 cell obtained by transferring the above expression vector into a tobacco BY-2 cells, steroid hormone-dependent transcription is induced, thereby enabling the amplification of mRNA of the GFP gene and induction of the expression of GFP.

5 Claims, 8 Drawing Sheets

(56) References Cited

OTHER PUBLICATIONS

Annual Report, No. 11, 2002, Laboratory of Plant Molecular Genetics, Research Institute of Agricultural Resources, Ishikawa Agricultural College, Dec. 26, 2003, pp. 13-15.
Lecture Summary, The 28th Annual Meeting of the Molecular Biology Society of Japan, Nov. 25, 2005.
Lecture Summary, The 22nd Symposium of Japanese Society for Plant Cell and Molecular Biology, Akita University, Aug. 8, 2004.
"Characterization of a human glycoprotein (erythropoietin) produced in cultured tobacco cells", S. Matsumoto et al., Plant Molecular Biology 27, 1995, pp. 1163-1172, © 1995 Kluwer Academic Publishers.
"Making an ally from an enemy: plant virology and the new agriculture", Gregory P. Pogue et al., Annu. Rev. Phytopathol. 2002, pp. 45-74, © 2002 by Annual Reviews.
"Transgenic plants as factories for biopharmaceuticals", G. Giddings et al., Nature Biotechnology, vol. 18, Nov. 2000, pp. 1151-1155, © 2000 Nature America, Inc.
"Production of enkephalin in tobacco protoplasts using tobacco mosaic virus RNA vector", N. Takamatsu et al., FEBS Letters, Aug. 1990, vol. 269, No. 1, pp. 73-76, © 1990 Federation of European Biochemical Societies.
"Auto-cleavable ribozyme sequence attached to brome mosaic virus cDNAs enchances accumulation of viral RNAs transcribed in vivo from the cDNAs", Masanori Kaido et al., Phytopatholigcal Note, Ann. Phytopathol, Soc. Jpn. 63 (2), Apr. 1997, pp. 95-98.
"Transfection of whole plants from wounds incolulated with *Agrobacterium tumefaciens* containing cDNA of tobacco mosaic virus", T.H. Turpen et al., Journal of Virological Methods 42 (1993), pp. 227-239.
"Tobamoviral Movement protein transiently expressed in a single epidermal cell functions beyond multiple plasmodesmata and spreads multicellularyly in an infection-coupled manner", Atsushi Tamai et al., Molecular Plant-Microbe Interactions, vol. 14, No. 2, 2001, pp. 126-134, © 2001 The American Phytopathological Society.
"Glucocorticoid-inducible expression of a bacterial avirulence gene in transgenic Arabidopsis induces hypersensitive cell death", T.W. McNellis et al., The Plant Journal (1998) 14(2), 247-257, © 1998 Blackwell Science Ltd.
"An estrogen receptor-based transactivator XVE mediates highly inducible gene expression in transgenic plants", J. Zuo et al., The Plant Journal (2000) 24(2), 265-273, © 2000 Blackwell Science Ltd.
"Ecdysone agonist inducible transcription in transgenic tobacco plants", A. Martinez et al., The Plant Journal (1999) 19(1), pp. 97-106, © 1999 Blackwell Science Ltd.
"Tobacco BY-2 Cell Line as the 'HeLa' Cell in the Cell Biology of Higher Plants", T. Nagata et al., International Review of Cytology (1992), vol. 132, pp. 1-30.
"A glucocorticoid-inducible transcription system causes severe growth defects in Arabidopsis and induces defense-related genes", H. Kang et al., The Plant Journal (1999) 20(1), pp. 127-133, © 1999 Blackwell Science Ltd.
Japanese Office Action mailed Jan. 25, 2005 by the Japanese Patent Office for the corresponding Japanese patent application No. 2003-350091.
Japanese Office Action mailed Jan. 25, 2005 by the Japanese Patent Office for the Japanese corresponding patent application No. 2004-056912.
"A specific cis-hairpin ribozyme facilitates infection of a TMV-based DNA vector in tobacco protoplasts", L. Wu et al., Journal of Virological Methods 111 (2003), pp. 101-109, © 2003 Elsevier B.V.
Shinmyo et al., "Molecular Improvement Technique for Plant Metabolic Engineering", Chapter 2, Section 2: Gene introducing technique, Handbook of Plant Metabolic Engineering, NTS Inc., pp. 236-243, (Jun. 25, 2002), with English translation.

\* cited by examiner

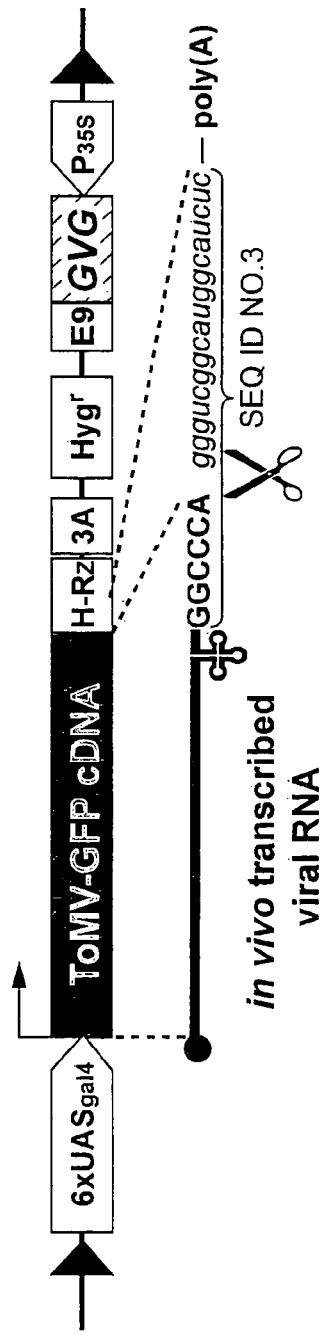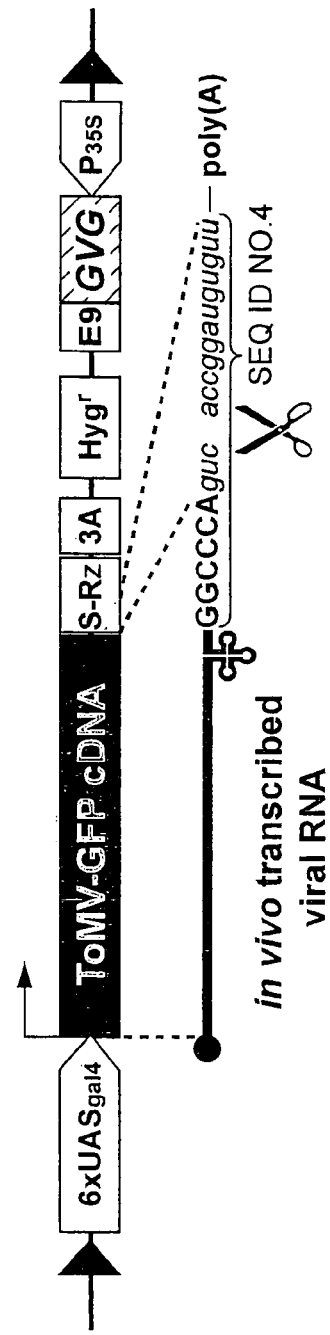
FIG. 5 (A)
FIG. 5 (B)

TOBACCO BY2 CELLS CONTAINING A TOMATO MOSAIC VIRUS VECTOR FOR PROTEIN PRODUCTION

TECHNICAL FIELD

The present invention relates to a transformed cell having incorporated an expression vector in which a gene of a plant virus having (i) a coding gene of a protein to be expressed, and (ii) a suppressor against a virus resistant reaction (silencing reaction) is ligated to an inducible promoter (for example, promoter induced by a chemical substance such as hormone). The invention also relates to a protein producing process using such a transformed cell, and a kit for performing such a protein producing process.

More specifically, the present invention relates to a transformed tobacco BY-2 cell having incorporated an expression vector in which a gene of a tomato mosaic virus (hereinafter, may be referred to as "ToMV") having (i) a coding gene of a protein to be expressed, and (ii) a suppressor against a virus resistant reaction (silencing reaction) is ligated to a promoter which is induced by steroid hormone. The invention also relates to a protein producing process using such a transformed tobacco BY-2 cell, and a kit for performing such a protein producing process.

Further, the present invention relates to a DNA fragment for expressing a virus vector, and use of such a DNA fragment.

More specifically, the present invention relates to (i) a DNA fragment in which a ribozyme sequence is ligated to the 3' end of cDNA of a virus vector that has incorporated a coding gene of an arbitrary protein, (ii) a vector containing the DNA fragment, and (iii) a transformant obtained by using such a DNA fragment or a vector.

The invention also relates to a process for reliably producing a transformant used for protein production and for inducing expression of a virus vector that has incorporated a coding gene of an arbitrary protein. The invention also relates to a protein-producing transformant produced by such a producing process, and use of such a transformant.

More specifically, the present invention relates to a process for producing a transformant for protein production, the process including: a first transforming step of transferring a transcription factor-expressing DNA fragment; a screening step of screening transformants, obtained in the first transforming step, for an individual expressing the transcription factor; and a second transforming step of transfecting the transformant, obtained in the screening step, with a protein-expressing DNA fragment. The invention also relates to a protein-producing transformant produced by such a producing process, and a protein producing process using such a protein-producing transformant.

BACKGROUND ART

In recent years, development of a producing process for efficient production of useful proteins such as pharmaceuticals has caught many interests. In this connection, there has been an ongoing development concerning use of plants not just as food but as factories for producing pharmaceuticals and other useful proteins. Such an effort is known as "molecular agriculture" and much is expected from this next-generation agriculture.

Currently, production of useful proteins in plants employs either a method using transgenic plants, or a method in which a plant is infected with a virus vector. (For details of the former, see Non-Patent Document 5: Transgenic plants as factories for biopharmaceuticals Glynis Giddings, Gordon Allison, Douglas Brooks & Adrian Carter Nature Biotechnology (2000) 18: 1151-1155.) (For details of the latter, see Non-Patent Document 1: Institute of Agricultural Sciences, Ishikawa Agricultural College, Annual Report, 2000, No. 9, 2000, pp. 16-18 (published on Oct. 25, 2001), and Non-Patent Document 2: Institute of Agricultural Sciences, Ishikawa Agricultural College, Annual Report, 2001, No. 10, 2001, pp. 13-16 (published on Sep. 25, 2002), and Non-Patent Document 9: Pogue G P, Lindbo J A, Garger S J, Fitzmaurice W P Making an ally from an enemy: Plant virology and the new agriculture. Annu Rev Phytopathol. 2002, 40: 45-74.)

Previously, the inventors of the present invention have constructed a gene expression system (hereinafter referred to as "high-level mRNA induction and amplification system"). In this system, a replicase gene of a plant virus (brome mosaic virus) and a useful protein gene amplified by the replicase gene are incorporated in the plant chromosomes, and the expression of the replicase gene is controlled for the synthesis of a useful protein. The high-level mRNA induction and amplification system was used in *Nicotiana benthamiana* plants, and expression of one of the subunits of the replicase, 1a protein, was induced by the steroid hormone control system. This enabled amplification of the gamma interferon gene at RNA level (see Non-Patent Documents 1 and 2).

Further, the inventors of the present invention constructed a steroid hormone-induced high-level mRNA amplification system for foreign proteins, in which tomato mosaic virus (ToMV), a member of the genus Tobamo mosaic virus, was used as a vector. ToMV is a highly replicative single strand RNA virus with a suppressor against a virus resistance reaction (silencing reaction). This system was used in *Nicotiana benthamiana* plants, and induced expression was attempted under the steroid hormone control system, using a green fluorescent protein gene (hereinafter "GFP gene") as a reporter gene. The result confirmed amplification of the gene at RNA level, as well as GFP expression (see Non-Patent Document 2).

Meanwhile, there have been attempts to produce useful proteins using plant culture cells. For example, there has been a report that a recombinant protein is produced in a tobacco BY-2 cell using the cauliflower mosaic virus 35S promoter (Non-Patent Document 3: Matsumoto S, Ikura K, Ueda M, Sasaki R. "Characterization of a human glycoprotein (erythropoietin) produced in cultured tobacco cells." Plant Mol boil. 1995 March; 27(6): 1163-72). In another example, protoplast tobacco BY-2 cells are inoculated with a variant virus RNA vector in which a target peptide gene has been ligated to the 3' end of a coat protein gene of tobacco mosaic virus (hereinafter "TMV"), so as to cause expression of a fusion protein fused with the coat protein (Non-Patent Document 4: Takamatsu N, Watanabe Y, Yanagi H, Meshi T, Shiba T, Okada Y. "Production of enkephalin in tobacco protoplasts using tobacco mosaic virus RNA vector." FEBS Lett. 1990 Aug. 20; 269(1): 73-6).

Among the foregoing protein producing methods in plants, the method using transgenic plants enables protein production by simple cultivation of plants. However, a problem of this method is that productivity of each cell is considerably poor. On the other hand, the method in which a plant is infected with a virus vector has good productivity but the method suffers from poor operability due to the inoculation procedure it requires. Another problem of the method is that mass production is difficult due to safety reasons, which includes viral spreading.

Referring to the high-level mRNA induction and amplification system constructed by the inventors with the brome mosaic virus, the brome mosaic virus does not have a suppressor against the virus resistance reaction (silencing reaction). Thus, when a recombinant virus is used that cannot form particles, the viral RNA is degraded by the silencing reaction (virus resistance reaction). That is, while the high-level mRNA induction and amplification system using brome mosaic virus allows a coding gene of the target protein to be amplified at RNA level, it cannot sustain high-level production of protein because the RNA is degraded overtime by the virus resistance reaction (silencing reaction). Another drawback of this system is that the transcription factor that was activated by steroid hormone causes etiolation or other undesirable effects, which is detrimental to plant growth.

The problem of RNA degradation can be avoided and the protein can be efficiently produced when the system using ToMV having a suppressor against the virus resistant reaction (silencing reaction) is used to produce protein in a plant. However, the system is associated with various problems: (1) Difficulties in producing protein on a large scale due to system requirements such as facilities for plant cultivation; (2) A relatively long time period for producing plants; (3) Safety problems posed by spreading of seeds or pollens, etc., of the transformed plants; and (4) Complex procedures.

As to the protein producing system using the tobacco BY-2 cells described in Non-Patent Documents 3 and 4, the system allows for protein production on cell culture, and is therefore suited for large-scale production. Further, the system offers fast amplification, which is advantageous when time is of concern. Another advantage is that the system is safe to use, owning to the fact that the cultured cells quickly die off even if the cells leak out of the system. However, methods based on this system still have the problem of poor productivity and the problem of complex procedure (forming protoplasts, inoculation), among others.

The inventors of the present invention have also developed a novel protein synthesis system (high-level mRNA induction and amplification system) that offers large-scale production with good productivity and good safety. A feature of the high-level mRNA induction and amplification system is that a viral replicase gene and a useful protein gene amplified by the replicase gene are incorporated in plant chromosomes, and that expression of the replicase in the recombinant plant is controlled to control synthesis of the useful protein (see Non-Patent Document 6: Mori, M., Fujihara, N., Mise, K. and Furusawa, I. (2001) Inducible high-level mRNA amplification system by viral replicase in transgenic plants. Plant J 27(1), 79-86).

Further, the inventors modified the foregoing high-level mRNA induction and amplification system with the use of a virus that has a suppressor against the silencing reaction of plants (see Non-Patent Document 2).

Meanwhile, the inventors of the present invention introduced a ribozyme sequence at the 3' end of viral cDNA, and produced a transformant with a tobacco plant. Transcription with the cauliflower mosaic virus 35S promoter enhanced viral RNA amplification as compared with a sample without the ribozyme (Non-Patent Document 7: Kaido, M., Mori, M., Mise, K., Okuno, T. and Furusawa, I. (1997) Auto-cleavable ribozyme sequence attached to brome mosaic virus cDNAs enhances accumulation of viral RNAs transcribed in vivo from the cDNAs. Ann. Phytopathol. Soc. Jpn. 63, 95-98). Further, by an *Agrobacterium* method, a tobacco plant was transfected with tobacco mosaic virus cDNA that has been appended with a ribozyme sequence at the 3' end. This almost doubled the infection rate (Non-Patent Document 8: Turpen, T. H., Turpen, A. M., Weinzettl, N., Kumagai, M. H. and Dawson W. O. (1993) Transfection of whole plants from wounds inoculated with *Agrobacterium tumefaciens* containing cDNA of tobacco mosaic virus. J. Virol. Methods. 42(2-3), 227-239).

In order to produce a useful arbitrary protein in plants, cultured tobacco BY-2 cells were transformed by the modified high-level mRNA induction and amplification system. However, only at most 5% of the cells showed virus amplification. The absence of virus amplification in most cells was considered to be due to a terminator-originating sequence and a poly-A sequence ligated to the 3' end of viral RNA transcribed from the cDNA in the cell. If this is indeed the case, further improvements need to be made in the high-level mRNA induction and amplification system, by removing the additional sequences attached to the 3' end of the viral RNA transcribed from the cDNA in the cell.

One way to remove the additional sequences attached to the 3' end of the viral RNA transcribed from the cDNA in the cell is to use the ribozyme described in Non-Patent Documents 7 and 8. However, Non-Patent Document 7 merely examines the extents of effects exerted by the presence or absence of ribozyme in regard to amplification of viral RNA, and it is not intended to express a foreign protein or use an inducible promoter. As to Non-Patent Document 8, no transformant is produced. Rather, the publication merely describes the result of temporary infection from cDNA using *Agrobacterium*. The report concludes that the addition of ribozyme almost doubles the infection rate. To this date, it has been believed that the effects of ribozyme sequence is limiting in the virus vector of the tobacco mosaic virus and other members of the genus Tobamovirus, and that it is not effective to add the ribozyme sequence for the purpose of causing protein production in the Tobamovirus vector.

As described above, the inventors of the present invention successfully improved the amplification rate of mRNA in the high-level mRNA induction and amplification system by using the virus that includes a suppressor against the silencing reaction of plants (Non-Patent Document 2 and Non-Patent Document 10: Institute of Agricultural Sciences, Ishikawa Agricultural College, Annual Report, 2002, No. 11 2002, pp. 14-15 (Published on Dec. 26, 2003).

Further, the inventors of the present invention have found that the ribozyme sequence added to the 3' end of the viral cDNA in the high-level mRNA induction and amplification system significantly enhanced the amplification of viral RNA as compared with the absence of the ribozyme sequence (for example, see Non-Patent Document 10).

A process for producing a foreign protein with the high-level mRNA induction and amplification system developed by the inventors of the present invention is excellent means for efficiently, inexpensively, and safely producing foreign proteins.

However, in producing (obtaining) transformants (cells), there are often cases where the expression level of virus vector and foreign protein differs between different lines of the resulting transformants (cells). Such a difference in expression level was considered to be due to the positions on the chromosome where the coding gene of the transcription factor and the coding gene of the virus vector are incorporated. More specifically, in the conventional virus vector transfer methods, a coding gene of the virus vector and a coding gene of the transcription factor are transferred into a host cell by being ligated to each other on the same vector. As such, these genes are incorporated in the same position of the chromosome.

However, it is not necessarily the case that the chromosomal locus suitable for the expression of the virus vector is also suitable for the expression of the transcription factor. For example, the genes may be incorporated in the chromosomal locus suitable for the expression of the virus vector but this particular locus may not be suitable for the expression of the transcription factor, and vice versa. In this case, the efficiency of induced expression conferred by the virus vector is low even if the cells have been transformed, and accordingly the expression level of foreign protein is also low.

Further, with current techniques, one must rely on chances as to the transfer position of the vector on the chromosome. For this reason, the probability that transformants (cells) expressing the virus vector and the target protein at high efficiency are obtained is considerably low, and large numbers of transformants (cells) need to be screened for a desirable transformant (cell) line. Thus, protein production using the high-level mRNA amplification system requires a large amount of time and labor.

DISCLOSURE OF INVENTION

As described above, conventional protein producing processes using plant and animal cells, and conventional protein producing systems have various problems and are not satisfactory.

The present invention was made in view of the foregoing problems, and an object of the present invention is to provide a protein producing system that has the advantages of protein production using transgenic plants and protein production using virus vectors. That is, the invention provides a protein producing system, and a protein producing process etc., capable of producing protein on a large scale with good productivity and good safety.

Further, the present invention was made in view of the foregoing problems, and an object of the present invention is make further improvements on the high-level mRNA induction and amplification system and therefore provide a system of transformed cell in which a virus vector that has incorporated a coding gene of an arbitrary protein can efficiently replicate through induced transcription.

Further, the present invention was made in view of the foregoing problems, and an object of the invention is to develop a process by which a transformant (cell) that can efficiently induce expression of the virus vector and express the target protein at high level is produced (obtained) with good probability, and thereby realize a protein producing process using the high-level mRNA induction and amplification system.

The inventors of the present invention diligently worked to solve the foregoing problems and accomplished the present invention by finding that reliable amplification of viral RNA and successful induction of GFP expression are possible when steroid hormone-dependent transcription was induced in transformed tobacco BY-2 cells that have incorporated an expression vector that has been constructed by introducing cDNA of recombinant ToMV, in which a coat protein gene has been substituted with a GFP gene, into the downstream side of a promoter capable of inducing transcription with a chemical substance such as steroid hormone.

Further, in accomplishing the present invention, the inventors added a ribozyme sequence in the tomato mosaic virus vector, a member of the genus Tobamovirus, for which addition of ribozyme has been believed to be ineffective. It was found as a result that the addition of a ribozyme sequence (i) cuts the additional sequences attached to the 3' end of viral RNA transcribed from the cDNA of the tomato mosaic virus vector in the cell, (ii) increases the viral RNA by a large amount, and (iii) results in a more than 10-fold increase for the percentage of cells expressing the green fluorescent protein-coding gene that has been transferred into the tomato mosaic virus vector.

Further, in accomplishing the present invention, the inventors of the present invention first produced (obtained) a transformant (cell) in which a coding gene of a transcription factor has been incorporated in the chromosomal locus most suited for the expression of the transcription factor, i.e., a transformant (cell) that can stably and efficiently produce the transcription factor, and then transfected the transformant with a virus vector that has incorporated a gene that encodes a target protein. This was found to be effective in efficiently inducing expression of the virus vector, and reliably producing (obtaining) transformants (cells) that can efficiently express the target protein.

Specifically, the present invention provides:

(1) A transformed cell constructed from a living cell that has incorporated an expression vector which includes: a gene of a plant virus having (i) a coding gene of a protein to be expressed, and (ii) a suppressor against a virus resistant reaction; and an inducible promoter ligated to the plant virus gene.

(2) A transformed cell as set forth in (1), wherein the plant virus is a tobamovirus.

(3) A transformed cell as set forth in (2), wherein the tobamovirus is one of tobacco mosaic virus and tomato mosaic virus.

(4) A transformed cell as set forth in any one of (1) through (3), wherein the inducible promoter is induced by a chemical substance.

(5) A transformed cell as set forth in (4), wherein the chemical substance is a hormone.

(6) A transformed cell as set forth in (5), wherein the hormone is a steroid hormone.

(7) A transformed cell as set forth in any one of (1) through (6), wherein the living cell is a plant cell.

(8) A transformed cell as set forth in (7), wherein the plant cell is a tobacco cell.

(9) A transformed cell as set forth in (8), wherein the tobacco cell is a tobacco BY-2 cell.

(10) A transformed cell as set forth in any one of (1) through (9), wherein the protein expression vector is transferred by an *Agrobacterium* method.

(11) A protein producing process, which uses the transformed cell of any one of (1) through (10).

(12) A protein producing process as set forth in (11), including a step of culturing the transformed cell.

(13) A protein producing process as set forth in (12), including a step of inducing transcription with a chemical substance.

(14) A protein producing process as set forth in (13), wherein the chemical substance used in the transcription inducing step of a hormone.

(15) A protein producing process as set forth in (14), wherein the hormone used in the transcription inducing step is a steroid hormone.

(16) A protein producing kit for performing a protein producing process of any one of (11) through (15).

(17) A protein producing kit as set forth in (16), including the expression vector of any one of (1) through (10).

(18) A protein producing kit as set forth in (16) or (17), including a hormone.

(19) A protein producing kit as set forth in (18), wherein the hormone is a steroid hormone.

(20) A protein producing kit as set forth in any one of (16) through (19), including a living cell which is used as a host.

(21) A protein producing kit as set forth in (20), wherein the living cell is a plant cell.

(22) A protein producing kit as set forth in (21), wherein the plant cell is a tobacco cell.

(23) A protein producing kit as set forth in (22), wherein the tobacco cell is a tobacco BY-2 cell.

(24) A DNA fragment for causing a cell to produce an arbitrary protein, the DNA fragment including: cDNA of a virus vector that has been constructed by inserting a coding gene of an arbitrary protein into an RNA virus; and a ribozyme sequence ligated to the 3' end of the virus vector cDNA.

(25) A DNA fragment as set forth in (24), wherein the virus vector originates in a virus that includes single strand (+) RNA.

(26) A DNA fragment as set forth in (24) or (25), wherein the virus vector originates in a plant virus.

(27) A DNA fragment as set forth in (26), wherein the virus vector originates in a plant virus that has a suppressor against a silencing reaction of plants.

(28) A DNA fragment as set forth in (27), wherein the virus vector originates in a tobamovirus.

(29) A DNA fragment as set forth in (28), wherein the virus vector is one of tobacco mosaic virus vector and tomato mosaic virus vector.

(30) A DNA fragment as set forth in any one of (24) through (29), wherein the ribozyme sequence is one of a ribozyme sequence of hepatitis delta virus and a ribozyme sequence of satellite tobacco ringspot virus.

(31) A DNA fragment as set forth in any one of (24) through (30), wherein the coding gene of an arbitrary protein is inserted into a downstream side of a promoter of a gene that encodes a coat protein of the virus.

(32) A DNA fragment as set forth in any one of (24) through (31), wherein the cDNA of the virus vector that has incorporated the coding gene of an arbitrary protein, and the ribozyme sequence ligated to the 3' end of the virus vector cDNA are transcribed under control of an inducible promoter that is located upstream of the virus vector cDNA and the ribozyme sequence.

(33) A DNA fragment as set forth in (32), including a gene that encodes a transcription factor for controlling transcription induced by the inducible promoter.

(34) A DNA fragment as set forth in (33), wherein the transcription is controlled by steroid hormone or estrogen.

(35) A DNA fragment as set forth in (34), wherein the transcription is controlled by (i) GVG, which is a transcription factor whose transcription inducing ability is activated by steroid hormone, and (ii) 6XUASga14, which is a promoter induced by activated GVG.

(36) A DNA fragment as set forth in (34), wherein the transcription is controlled by (i) XVE, which is a transcription factor whose transcription inducing ability is activated by estrogen, and (ii) $O_{LexA}$-46, which is a promoter induced by activated XVE.

(37) A vector, which includes the DNA fragment of any one of (24) through (36), and has an ability to be incorporated in a cell genome.

(38) A vector as set forth in (37), wherein the vector is a Ti plasmid.

(39) A transforming kit, which includes the DNA fragment of any one of (24) through (36), and/or the vector of (37) or (38).

(40) A transformant, which is obtained with use of one of (i) the DNA fragment of any one of (24) through (36), (ii) the vector of (37) or (38), and (iii) the transforming kit of (39).

(41) A transformant in which a virus vector is transcribed and expressed, and which is obtained with use of (i) a DNA fragment in which a ribozyme sequence is ligated to the 3' end of a virus vector that has incorporated a coding gene of an arbitrary protein, or (ii) a vector which includes the DNA fragment.

(42) A transformant in which a virus vector originating in a tobamovirus is transcribed and expressed, and which is obtained with use of (i) a DNA fragment in which a ribozyme sequence is ligated to the 3' end of a tobamovirus vector that has incorporated a coding gene of an arbitrary protein, or (ii) a vector which includes the DNA fragment.

(43) A transformant as set forth in (42), wherein the transformant is a plant or a cultured cell.

(44) A transformant in which a virus vector is transcribed and expressed, and which is obtained with use of (i) a DNA fragment in which a ribozyme sequence is ligated to the 3' end of a virus vector that has incorporated a coding gene of an arbitrary protein, and which is capable of inducing transcription of the virus vector, or (ii) a vector which includes the DNA fragment.

(45) A protein producing process, which uses the transformant of any one of (41) through (44).

(46) A process for producing a transformant for protein production, including: a first transforming step of transfecting a host cell with a transcription factor-expressing DNA fragment in which a coding gene of a transcription factor is ligated to a promoter for expressing the transcription factor; a screening step of screening transformants, obtained in the first transforming step, for an individual expressing the transcription factor; and a second transforming step of transfecting the transformant, obtained in the screening step, with a protein-expressing DNA fragment in which cDNA of a virus vector that has been constructed by inserting a coding gene of an arbitrary protein into an RNA virus is ligated to an inducible promoter which is induced by the transcription factor.

(47) A process for producing a transformant for protein production as set forth in (46), wherein the transcription factor has a property of being activated by hormone.

(48) A process for producing a transformant for protein production as set forth in (47), wherein the hormone is estrogen or steroid hormone.

(49) A process for producing a transformant for protein production as set forth in (48), wherein LexA-VP16-hER is used as the transcription factor having a property of being activated by estrogen, and wherein $O_{LexA}$-46 is used as the inducible promoter.

(50) A process for producing a transformant for protein production as set forth in any one of (46) through (49), wherein the virus vector originates in a virus that includes single strand (+) RNA.

(51) A process for producing a transformant for protein production as set forth in (50), wherein the virus vector originates in a plant virus.

(52) A process for producing a transformant for protein production as set forth in (51), wherein the virus vector originates in a plant virus that has a suppressor against a silencing reaction of plants.

(53) A process for producing a transformant for protein production as set forth in (52), wherein the virus vector originates in a tobamovirus.

(54) A process for producing a transformant for protein production as set forth in (53), wherein the virus vector is one of tomato mosaic virus and tobacco mosaic virus.

(55) A process for producing a transformant for protein production as set forth in any one of (46) through (54), wherein a ribozyme sequence is ligated to the 3' end of the virus vector cDNA.

(56) A process for producing a transformant for protein production as set forth in (55), wherein the ribozyme sequence is one of (i) a ribozyme sequence of hepatitis delta virus, and (ii) a ribozyme sequence of satellite tobacco ringspot virus.

(57) A process for producing a transformant for protein production as set forth in any one of (46) through (56), wherein the coding gene of an arbitrary protein is substituted with a gene that encodes a coat protein of the virus.

(58) A process for producing a transformant for protein production as set forth in any one of (46) through (57), wherein the transcription factor-expressing DNA fragment and the protein-expressing DNA fragment are transferred by an *Agrobacterium* method.

(59) A process for producing a transformant for protein production as set forth in any one of (46) through (58), wherein the host cell and the transformant are plants or plant culture cells.

(60) A process for producing a transformant for protein production as set forth in (59), wherein the plant culture cells are tobacco cells.

(61) A process for producing a transformant for protein production as set forth in (60), wherein the tobacco cells are tobacco BY-2 cells.

(62) A transformant for protein production, which is produced by the process for producing a transformant for protein production as set forth in any one of (46) through (61).

(63) A protein producing process, which uses the transformant for protein production as set forth in (62).

(64) A producing kit for performing the process for producing a transformant for protein production as set forth in any one of (46) through (63).

For a fuller understanding of the nature and advantages of the invention, reference should be made to the ensuing detailed description taken in conjunction with the accompanying drawings.

BRIEF DESCRIPTION OF DRAWINGS

FIGS. 5(A) and 5(B) are schematic views showing structures of vectors used in Example, in which FIG. 5(A) schematizes a vector to which a ribozyme sequence (H-Rz) of hepatitis delta virus has been added, and FIG. 5(B) schematizes a vector to which a ribozyme sequence (S-Rz) of satellite tobacco ringspot virus has been added.

FIGS. 6(A) through 6(C) are observed images of induced GFP expression in the transformed BY2 cells under a fluorescent microscope, in which FIG. 6(A) represents cells transformed with a control vector, FIG. 6(B) represents cells transformed with the vector to which the ribozyme sequence of hepatitis delta virus was added, and FIG. 6(C) represents cells transformed with the vector to which the ribozyme sequence of satellite tobacco ringspot virus was added.

BEST MODE FOR CARRYING OUT THE INVENTION

Figure 1:
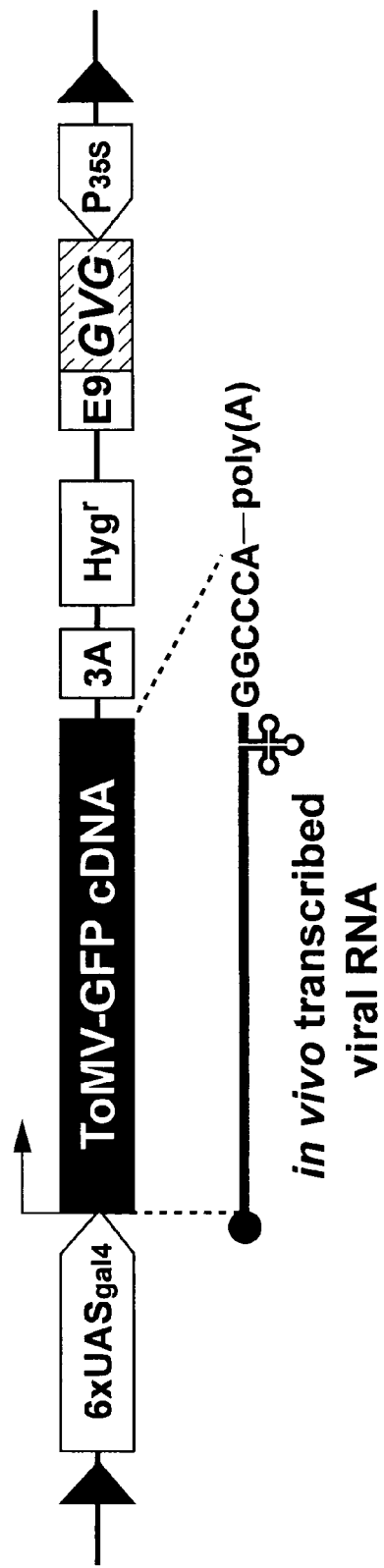
FIG. 1 is a schematic view illustrating a structure of pTA7001-ToMV-erG3(SF3) as one example of an expression vector introduced into a transformed cell according to the present invention.

The following will describe one embodiment of the present invention. It should be noted here that the invention is not limited in any way by the following description.

First, description is made as to (A) a transformed cell (hereinafter "transformed cell according to the invention") that is obtained from a living cell having incorporated therein an expression vector which has been constructed by legating (i) a gene of a plant virus having a gene that encodes a protein to be expressed and having a suppressor against a virus resistant reaction (silencing reaction) to (ii) a promoter for inducing hormone-induced transcription; (B) a process for producing a protein using the transformed cell (hereinafter "protein producing process according to the present invention"); and (C) a kit for performing the protein producing process (hereinafter "protein producing kit according to the present invention").

(A) Transformed Cell of the Invention

A transformed cell according to the present invention is obtained from a living cell having incorporated therein an expression vector which has been constructed by ligating (i) a gene of a plant virus having a gene that encodes a protein to be expressed and having a suppressor against a virus resistant reaction (silencing reaction) to (ii) a promoter for inducing hormone-induced transcription.

<Plant Virus Having a Suppressor Against Virus Resistant Reaction>

The virus resistant reaction (silencing reaction) is a reaction that works to efficiently eliminate RNA that is aberrant to living activities. The virus resistant reaction is found broadly throughout many living organisms, including nematodes (*C. elegans*), fruit flies (*D. melanogaster*), mice, humans, and plants. Briefly, it is a defense mechanism against viral infection.

More specifically, viral infection leads to large production of undesirable viral RNA (mRNA, genomic RNA of the virus) in the infected cell. In response, the infected cell generates a virus resistant reaction (silencing reaction) to destroy the viral RNA and thereby prevent spread of viral infection.

As a countermeasure, many viruses have the ability to suppress the viral resistant reaction (silencing reaction) of the cells. Specifically, the virus expresses a suppressor (suppressing factor) against the suppressing action of the virus resistant reaction (silencing reaction).

A transformed cell of the present invention is obtained by transferring an expression vector that includes a gene of a plant virus, and it is used for the expression of a target protein contained in the vector. The virus is therefore required to have a suppressor against the virus resistant reaction (silencing reaction).

If a plant virus used in the present invention did not have a suppressor, then, as described in the BACKGROUND ART section, amplified mRNA of a gene of a target protein is degraded over time by the virus resistant reaction (silencing reaction), with the result that sustained production of protein cannot be carried out.

It is therefore preferable that a plant virus used in the present invention include a suppressor.

Non-limiting examples of a suppressor-containing plant virus include those belonging to: genus Potyvirus; genus Cucumovirus (e.g., cucumber mosaic virus ("CMV")); genus Potexvirus (e.g., potato virus X ("PVX")); genus Tombusvirus (e.g., tomato bushy stunt virus ("TBSV")); genus Cymbidiumu ringspot virus ("CymRSV")); genus Carmovirus (e.g., turnip crinkle virus ("TCV"); genus Tobamovirus (e.g., tobacco mosaic virus ("TMV"), tomato mosaic virus ("ToMV")).

In the Examples to be described later, expression vectors were constructed using ToMV because the virus (i) is more proliferative than other viruses and therefore offers mass production of protein, (ii) is highly proliferative in tobacco BY-2 cells used in Examples, and (iii) has been widely used due to good ease of handling, versatility, and applicability.

With a plant virus having a suppressor, the amplified mRNA of the target protein will not be degraded by the virus resistant reaction (silencing reaction), and the protein can be produced both continuously and efficiently.

As used herein, the "plant virus" is a collective term for viruses which use plants as hosts. In the narrow sense, it refers to viruses in higher plants. Plants infected with viruses show various symptoms such as mosaic, chlorosis, etiolation, malformation, leaf-curling, dwarfing, and necrosis, depending on the type of virus and the type of plant infected by the virus. This poses serious damage to the crops and harvesting. The virus may be fluid-borne, insect-borne, soil-borne, graft-borne, or seed-borne. Some viruses proliferate within an insect vector and spreads through ovarial transmission.

<Construction of Expression Vector>

The target protein to be expressed is not particularly limited as long as it is expressable in a living cell. Some of the examples include: enzymes usable as medicaments; interferons; allergic proteins; antigens for pathogens; erythropoietin; enkephalin; cell growth factors; antibodies (immunoglobulins); and albumins. By taking protein-expressing cells in an appropriate dose, the cells can be used as a medicament with the action equivalent to taking the protein alone.

For the transfer a gene that encodes a target protein to be expressed, common genetic engineering techniques can be used, for example, such as substitution with part of genes of the plant virus having a suppressor, or ligation to the viral gene.

In order to construct the expression vector transferred into the transformed cell of the present invention, a gene of the recombinant plant virus that has incorporated a gene that encodes the target protein is ligated to the downstream side of an inducible promoter. With the inducible promoter, the expression of the plant virus protein can be efficiently induced downstream of the promoter.

The inducible promoter and the vehicle vector of the promoter are not particularly limited and may be selected from conventional promoters and vectors.

As an example, a promoter capable of inducing chemical- or temperature-dependent transcription can be used. Such promoters are well known in the art in a wide variety of eukaryotes (both plant and animal cells), and can be suitably used in the present invention. Examples of such promoters include those induced by chemicals (tetracycline), hormones, glucocorticoids, and metals (including metal ions), and those induced by heat shock.

Among these examples, promoters induced by hormone are particularly preferable, as will be described later in Examples. Suitable examples include: pTA7001 (Stu), which was constructed by the inventors of the present invention from Ti plasmid pTA7001 that includes a promoter which is induced by steroid hormone (see McNellis T W, Mudgett M B, Li K, Aoyama T, Horvath D, Chua N H, Staskawicz B J. Glucocorticoid-inducible expression of a bacterial avirulence gene in transgenic *Arabidopsis* induces hypersensitive cell death. Plant J. 1998 April; 14(2):247-57); and Ti plasmid pER8, which includes a promoter which is induced by estrogen (see Zuo, J., Niu, Q. W., and Chua, N. H. (2000). An estrogen receptor-based transactivator XVE mediates highly inducible gene expression in transgenic plants. Plant J. 24, 265-273). As examples of vectors used for transformation, plasmids pES60 and pES46 including a promoter which is induced by ecdysone are available (The Plant Journal (1999) 19: 97-106. Ecdysone agonist inducible transcription in transgenic tobacco plants Alberto Martinez, Caroline Sparks, Cliff A. Hart, John Thompson and Ian Jepson).

It is preferable that the expression vector includes a transcription factor for the promoter. The transcription factor allows for transcriptional control of the plant virus gene ligated downstream of the promoter. This is advantageous in inducing transcription more efficiently. The transcription factor can be selected according to the type of promoter used. For example, transcription factor GVG is used for the Ti plasmid pTA7001 (Stu) including the promoter induced by steroid hormone, and XVE is used for the Ti plasmid pER8 including the promoter induced by estrogen.

The expression vector may additionally include various kinds of DNA segments, for example, such as a terminator. Further, for the expression of chimeric proteins, the expression vector may include, as required, genes that encode other proteins, or restriction enzyme recognition sites (for example, multiple cloning sites) for incorporating such genes.

The method of constructing the expression vector (preparation method) is not limited to a specific method.

Conventional recombinant DNA techniques can be used to bind the vehicle vector to DNA segments such as the recombinant virus genes and the promoter. The amplification method of the expression vector (producing method) is not limited either and conventional method can be used. Generally, *E. coli* is used as a host, and the expression vector is amplified therein. The type of *E. coli* may be suitably selected according to the type of vector used.

<Transformation Method>

The method by which the expression vector is introduced into the plant host cell is not particularly limited, and a transformation method is suitably selected according to the type of plant host cell. A common transformation method used for plant cells is the transformation method using *Agrobacterium* (*Agrobacterium* method). The present invention can suitably use the *Agrobacterium* method, as will be described later in Examples. Other conventional methods suitable in the invention include: a particle gun method; a protoplast/spheroplast method; an electroporation method; a calcium phosphate method; a liposome method; and a DEAE dextran method, for example.

The method of confirming whether the recombinant plant virus gene (expression vector) has been incorporated in the host cell or successfully expressed therein is not limited to a particular method and a variety of conventional methods can be used therefor. Specifically, various markers can be used. For example, a gene lacking in the host cell is used as a marker, and a plasmid or the like containing the marker and the recombinant plant virus gene is introduced as an expression vector into the host cell. Successful transfer of the gene of the present invention can be confirmed by the expression of the marker gene.

In the Examples to be described later, a drug-resistant marker (hygromycin-resistant marker Hygr) is used, for example. Potential strains of transformants are cultured in a hygromycin-containing medium, which then allows for screening of transformants from the cultured cell lines. Other examples of drug-resistant markers that are effective for the screening of plant cells include bialaphos-resistant marker and kanamycin-resistant marker. For the screening of animal cells, the following markers and genes are effective: puromycin-resistant marker, bleomycin-resistant marker, XGPRT gene, DHFR gene, and thymidine kinase-resistant marker. In yeasts, auxotrophic markers such as a uracil auxotrophic marker can be used for screening. The screening method of transformants is not limited and may be suitably selected depending on the type of host transfected with the expression vector.

Alternatively, a genomic PCR method may be used in which a total length gene of the transferred protein in the transfected host is specifically amplified, using the genomic DNA of the host cell as a template. With this method, successful transfer of the gene can be conformed if amplification of the gene that encodes a target protein were confirmed by electrophoresis or the like.

As yet another method, the target protein may be expressed as a fusion protein. For this purpose, the green fluorescent protein derived from belt jellyfish (*Aequorea coerulescens*) may be used as a marker, for example. Further, the expression vector may include a gene that visualizes expression sites in the transformed cells and thereby allows one to monitor these expression sites. As an example, β-glucuronidase (GUS) gene is available.

<Host Cell>

The host cell transfected by the expression vector is not particularly limited as long as it is obtained from living organisms, which may be plants or animals. However, plant cells are more preferable than animal cells for reasons that plant cells grow more rapidly and therefore have a lower risk of contamination, and that the cost of culture media is considerably cheaper. As used herein, the "animal cells" and "plant cells" refer to cells, tissues, and organs derived from animals or plants, excluding animals and plants themselves. Of these, cells that can grow in, for example, a liquid medium is particularly preferable.

Non-limiting examples of animals include: human; monkey; dog; sheep; goat; rabbit; mouse; rat; guinea pig; Chinese hamster; cattle; horse; pig; fishes such as ricefish and zebrafish; silkworm; fall armyworm (*Spodoptera frugiperda*).

Non-limiting examples of plants include: rice; mouseear cress (*Arabidopsis thaliana*); barley; wheat; tobacco; tomato; cucumber; soy bean; potato; corn; vinca (*Catharanthus roseus*); mouseear cress (*Arabidopsis thaliana*); and alfalfa.

Other than plant and animal cells, bacteria such as *bacillus subtilis* and lactic acid bacteria, or unicellular cells such as yeasts may be used as host cells.

Non-limiting examples of animal cells include: HeLa cell; CHO cell; melanoma cell; and mouse 3T3 cell. Non-limiting examples of plant cells include: tobacco BY-2 cell; potato cell; rice cell; sweet potato cell; soy bean cell; parsley cell; mouseear cress cell; wheat cell; corn cell; and vinca cell.

In the Examples to be described later, the BY-2 tobacco cell is used as a host. The tobacco BY-2 cell was used because it is the most widely cultured plant cell line in the world, and because it has the fastest growth rate, allows for easy genetic manipulation, and can be cultured in mass quantity. For details of tobacco BY-2 cells, see Toshiyuki Nagata, Yasuyuki Nemoto, and Seiichiro Hasezawa "Tobacco BY-2 Cell Line as the "Hela" Cell in the Cell Biology of Higher Plants" International Review of cytology, vol. 132, p.p. 1-30 (1992)).

In the present invention, plant cells, rather than plants themselves, are used as host cells. This is because plant cells offer the following advantages.

(a) Compared with plants used as hosts, plant cells have a faster growth rate and can produce transformed cells in a shorter time period. Plant cells are also advantageous in terms of large-scale and mass production.

(b) Compared with plants used as hosts, plant cells can grow in much smaller space, and do not require facilities, for example, such as a field or a green house, for growth. Further, plant cells conveniently allow for use of a large incubator.

(c) Compared with plants used as hosts, plant cells do not require the step of differentiating a callus into individual plants, the step of obtaining seeds from a flower, and the step of growing plants from seeds. Therefore, plants cells require a much shorter time period for the preparation of transformants, screening, and protein production.

(d) With plant cells, expression of a protein can easily be induced using a chemical substance or other inducers. When plants are used as hosts, a chemical substance or other inducers needs to be uniformly applied over the plants by a method, for example, such as direct application or spraying. This is very tedious and time consuming. In contrast, with plant cells, the inducer only needs to be added to the cell culture. This allows the cells to induce protein expression both simultaneously and uniformly.

(e) In plants, precise temperature control of the plant surface is difficult due to the transpiration or other activities of the plants. Such temperature control is easier when plant cells are used that grow in a liquid medium. Further, when used with a promoter that is highly sensitive to various stresses such as changes in environment conditions, plant cells allows for stable production of protein.

(f) Unlike the plants made up of various tissues, the cultured cells are homogenous. This makes it easier to control protein expression because the tissue-specific effects can be ruled out.

(g) Because the cell cycles can be synchronized in a sophisticated manner, protein expression can be precisely controlled.

(h) Because a liquid medium is used, secretory proteins released in the media can be collected and purified easily. Even non-secretory target proteins can be collected and purified just as easily when the proteins are appended with secretory tags.

(i) Since the cultured cells, unlike plants themselves, do not require light to grow, the size of lighting equipment and the cost of lighting can be reduced. This is also advantageous in expressing photo-sensitive proteins.

(j) The proteins produced in the medium can be chemically modified by adding various kinds of chemical substances in the medium. For example, by adding radioactive isotopes, radioactively labeled proteins can be easily produced.

(k) Plant cells are safer to use because the transformed cells, unlike the plants themselves, cannot grow by themselves and die off when they leak out of the system. This is advantageous in terms of equipment, cost, and time required for the risk management concerning the spread of plant individuals, seeds, and pollens, as well as the risk management for safety tests and genetically modified organisms.

(B) Producing Process of a Protein According to the Present Invention

A protein producing process according to the present invention uses the transformed cell of the present invention. A protein producing step according to the present invention may be adapted so that the product protein in the cell is obtained without culturing the transformed cells obtained by the transformation. However, it is preferable that a protein producing process according to the present invention include the step of culturing the transformed cells of the invention (hereinafter "cell culturing step"). By the culturing step, the number of transformed cells having incorporated a gene that encodes a target protein can be increased, with the result that the amount of product protein can also be increased.

The method of culturing the cells in the cell culturing step is not particularly limited. The cells can be cultured in a suitable medium and under suitable conditions. The type of medium used to culture the plant cells is not particularly limited, and it may optionally contain inorganic salts, carbon source, vitamins, and amino acids. Additionally, the culture medium may be supplemented with coconut milk or yeast extracts to promote growth. Further, plant hormones such as auxin/cytokinin, gibberellin, abscisic acid, and ethylene may be added. Culture conditions such as light, temperature, and the presence or absence of aeration can be suitably set according to the type of cultured cell. For example, in the Examples to be described later, tobacco BY-2 cells were cultured in MS medium containing 370 mg/l of potassium dihydrogen phosphate, 1 mg/l of thiamine hydrochloride, 3% sucrose, and 0.2 mg/l of 2,4-D. The cells were cultured in dark at 26° C. using a rotary incubator (135 revolutions per minute), and a subculture (1/100) was made every week.

The type of medium used to culture the animal cells is not particularly limited either, and it may optionally contain a serum with amino acids, vitamins, glucose, and salts. As the buffer solution, a solution of bicarbonate/carbonate gas is used, and a $CO_2$ incubator is used as the incubator. In order to monitor pH, phenol red may be added. Generally, the cells are cultured at 37° C. Depending on the cell line, the cells may be cultured at 28° C. or 40° C.

It is preferable that a protein producing process according to the present invention include, in addition to the cell culturing step, the step of inducing chemical-dependent transcription, particularly hormone- (for example, estrogen) dependent transcription in the cultured cells (hereinafter "transcription inducing step"). The expression vector transferred into a transformed cell of the present invention includes a promoter for inducing hormone-dependent transcription. Thus, in the transcription inducing step, the promoter can start transcription of a gene that encodes a target protein, and increase the amount of transcripts in a controlled manner, among other things. It is therefore possible to increase and control the amount of product protein.

The hormone used in the transcription inducing step is not particularly limited and can be suitably selected according to the type of promoter included in the expression vector that is transferred into a transformed cell of the present invention. Examples include steroid hormone, estrogen, and ecdysone.

In the Examples to be described later, in order to construct a protein expression vector, Ti plasmid pTA7001 (Stu) having a promoter that induces steroid hormone-dependent transcription is used as a vehicle. As such, steroid hormone was used to induce transcription.

The amount of hormone used in the transcription inducing step is suitably selected according to the type of promoter, the type of cell line, the culture phase of the cell line used, and the culture conditions of the cells, for example. In the Examples to be described later, 30 μM steroid hormone (dexamethasone) was used in the transcription inducing step, for example.

The time of the transcription inducing step is not particularly limited, and it may be suitably selected according to the type of cell line, the culture phase of the cell line used, and culture conditions of the cells, for example. For example, in the Examples to be described later, the percentage of cells expressing the GFP, reporter proteins, was the highest when the transcription was induced 5 days post subculture. It was found from the result that, under the conditions used in Examples below, the physiological conditions of the cultured cells on day 5 of the pre-culture were suitable for the induction of transcription and the expression of protein.

(C) Protein Producing Kit According to the Present Invention

A protein producing kit according to the present invention is not particularly limited as long as it includes reagents, instruments, equipment, and the like that can be used to perform the protein producing process of the present invention. Preferably, the protein producing kit includes the expression vector that is transferred into a transformed cell of the present invention. In this case, a gene that encodes a target protein to be expressed is transferred into the expression vector by ordinary genetic modification techniques such as ligation and substitution. This allows for production of the target protein.

For example, the protein producing kit may include an expression vector that has been constructed by introducing cDNA of genetically modified ToMV, in which the coat protein gene has been substituted with GFP gene, into the downstream side of the promoter capable of inducing steroid hormone-dependent transcription. In this case, the GFP gene may be substituted with the gene of a target protein to be expressed, or the target protein gene may be ligated to the GFP gene. In the case where the target protein gene is ligated to the GFP gene, the target protein is obtained as a fusion protein fused with GFP, and the protein can be produced by monitoring its expression with the use of GFP fluorescence as an indicator.

It is also preferable that a protein producing kit according to the present invention includes a hormone for performing the transcription inducing step. The hormone included in the protein producing kit can be suitably selected according to the type of promoter included in the expression vector that is transferred into a transformed cell of the present invention. Examples include steroid hormone, estrogen, and ecdysone.

In the case where Ti plasmid pTA7001 (Stu) having a promoter for inducing steroid hormone-dependent transcription is used as a vehicle to construct the protein expression vector, the protein producing kit preferably includes steroid hormone.

A protein producing kit according to the present invention may further include living cells to be used as hosts. The host cell included in the protein producing kit is not particularly limited as long as it is obtained from living organisms, which may be plants or animals. Non-limiting examples of animals include human; monkey; dog; sheep; goat; rabbit; mouse; rat; guinea pig; Chinese hamster; cattle; horse; pig; fishes such as ricefish and zebrafish; silkworm; fall armyworm (*Spodoptera frugiperda*).

Non-limiting examples of plants include: rice; mouseear cress (*Arabidopsis thaliana*); barley; wheat; tobacco; tomato;

cucumber; soy bean; potato; corn; vinca (*Catharanthus roseus*); mouseear cress (*Arabidopsis thaliana*); and alfalfa.

Other than plant and animal cells, bacteria such as *bacillus subtilis* and lactic acid bacteria, or unicellular cells such as yeasts may be used as host cells.

Non-limiting examples of animal cells include: HeLa cell; CHO cell; melanoma cell; and mouse 3T3 cell. Non-limiting examples of plant cells include: tobacco BY-2 cell; potato cell; rice cell; sweet potato cell; soy bean cell; parsley cell; mouseear cress cell; wheat cell; corn cell; and vinca cell.

A protein producing kit according to the present invention may additionally include, for example, a culture medium and an incubator for culturing the cells.

As is clear from the foregoing description, it will be possible with the present invention to provide a large-scale, highly efficient, and safe system of producing proteins. The invention can also provide a protein producing process and the like.

In the following, description is made as to (D) a high-level mRNA induction and amplification system, (E) a DNA fragment of the present invention, and a vector including it, (F) a plant cell transforming kit, and (G) a transformant and a protein producing process, in this order.

(D) High-Level mRNA Induction and Amplification System

For the production of useful proteins, the inventors of the present invention constructed a high-level mRNA induction and amplification system, which is a large-scale, highly efficient, and safe system of synthesizing proteins. The following briefly outlines the inventors' high-level mRNA induction and amplification system that uses the brome mosaic virus (see Non-Patent Document 6). The brome mosaic virus replicates rapidly, and genes are contained in single-strand (+) RNA. The RNAs contained in the brome mosaic virus include RNA1 and RNA2 that encode 1a and 2a proteins of the replicase, respectively, and RNA3 that encodes 3a protein required for intercellular and whole movement. RNA3 also encodes a coat protein. The coat protein is the product of translation of the mRNA that is synthesized from the RNA3 (−) strand by the replicase of the virus. The cDNA of RNA1, the cDNA of RNA2, and the cDNA of chimeric RNA3, in which the coat protein gene has been substituted with a gene that encodes a useful protein, were transferred into different plant cells, so as to produce transgenic plants with three kinds of viral RNA genes. The RNA2 and chimeric RNA3 were expressed at all times using a cauliflower mosaic virus 35S promoter, whereas expression of RNA 1 was controlled by a promoter that induces steroid hormone-dependent transcription. As a result, a high-level mRNA induction and amplification system was constructed in which the viral replicase was produced and the mRNA of the target protein was amplified only when there was a steroid hormone treatment.

Features of the high-level mRNA induction and expression system are as follows:

(1) The mRNA of useful protein can be expressed very efficiently:

(2) The expression of useful protein can be induced in a controlled manner;

(3) By the expression control, the system allows for synthesis of a protein that is toxic to plant growth;

(4) The system is very safe to use because it can suppress expression in an open system such as a farm field, and induce expression in a closed system such as a factory; and (5) Due to the lack of coat protein, the viral gene that is transferred for amplification cannot infect other plants or form particles.

However, in the brome mosaic virus system, there is notable degradation of mRNA in the second half of amplification. A plausible explanation for this is that the brome mosaic virus does not have a suppressor against the virus resistance (silencing) of the plant. To find out, the inventors of the present invention constructed a high-level mRNA induction and amplification system using tomato mosaic virus (hereinafter may be referred to as "ToMV"), which is a highly replicative single-strand (+) RNA virus with the silencing suppressor. As used herein, the term "silencing" refers to a plant defense mechanism against viruses, and it also refers to the phenomenon in which expression of foreign genes are suppressed.

With the use of the tomato mosaic virus instead of the brome mosaic virus, no degradation of mRNA occurred in the second half of amplification. However, in an attempt to construct a ToMV high-level mRNA induction and amplification system in cultured tobacco BY2 cells, the virus vector was amplified in at most 5% of the cells, i.e., amplification of the virus vector was not observed in most cells. This was considered to be due to addition of a terminator-derived sequence and a poly-A sequence at the 3' end of the viral RNA that was transcribed from the cDNA in the cell. Based on this reasoning, the inventors of the present invention constructed a DNA fragment by adding a ribozyme sequence at the 3' end of the virus vector cDNA. The term "ribozyme" refers to an RNA molecule with the enzyme activity. As used herein, the term also refers to RNA that catalyzes self-cleaving reaction. With the use of such a vector, the additional sequences at the 3' end of the viral RNA transcribed from the cDNA in the cell are cut, with the result that the percentage of cells with amplified viral RNA is greatly increased.

(E) DNA Fragment according to the Present Invention, and a Vector Including the DNA Fragment A DNA fragment according to the present invention is used to produce an arbitrary protein in a cell. Necessary constituents of the DNA fragment at least include: cDNA of an RNA virus vector in which a gene that encodes an arbitrary protein to be produced in the cell has been inserted; and a ribozyme sequence bound to the 3' end of the virus vector cDNA. The type of arbitrary protein produced in the cell is not particularly limited. It may be a useful foreign protein, or a protein that originates in the plant itself. For example, a human protein usable as a medicament is suitable.

The virus vector is not particularly limited as long as it is obtained from an RNA virus. For example, the virus vector may be obtained from a double strand RNA virus, a single strand (−) RNA virus, and a single strand (+) RNA virus. Among these examples, the single strand (+) RNA virus is particularly preferable because the RNA that is transcribed from the cDNA in the cell directly serves as mRNA. Further, since the single strand (+) RNA virus replicate rapidly, the target protein can be produced efficiently.

The virus vector is not limited to those derived from animal viruses, and various types of virus vectors can be used that are derived from various RNA viruses, including animal viruses and phages. For the purpose of producing an arbitrary protein in plant cells, a virus vector derived from a plant virus is preferably used. Particularly, a virus vector derived from a virus having a suppressor against the silencing of the plant is preferable. With the use of the virus vector having the silencing suppressor, there will be no degradation of mRNA in the second half of amplification. Examples of plant viruses having the silencing suppressor include those belonging to: genus Potyvirus; genus Cucumovirus (e.g., cucumber mosaic virus ("CMV")); genus Potexvirus (e.g., potato virus X ("PVX")); genus Tombusvirus (e.g., tomato bushy stunt virus ("TBSV")); genus Cymbidiumu ringspot virus ("CymRSV")); genus Carmovirus (e.g., turnip crinkle virus ("TCV"); genus Tobamovirus (e.g., tobacco mosaic virus ("TMV"), tomato mosaic virus ("ToMV")).

The ribozyme sequence used in the DNA fragment of the present invention is not particularly limited as long as it can cut the additional sequences ligated to the 3' end of the viral RNA that was transcribed from the virus vector cDNA that has incorporated a gene for encoding an arbitrary protein. For example, the ribozyme sequence of hepatitis delta virus or satellite tobacco ringspot virus may be used.

With the ribozyme sequence, the terminator-derived sequence and the poly-A sequence can be cut that are added to the 3' end of the viral RNA transcribed from the cDNA in the cell and that are detrimental to the replication of the virus. As a result, the replicating ability of the virus does not suffer, and the foreign protein can be produced efficiently.

It is preferable that a gene that encodes an arbitrary protein be inserted downstream of the promoter for a gene that encodes the coat protein of the virus, and more preferably be substituted with a gene that encodes the coat protein of the virus. With the gene inserted at these sites, there will be no production of the viral coat protein, and the amplified viral gene will not form particles and infect other plants, thereby solving the problem of viral spreading. Further, since the promoter for the gene that encodes the coat protein of the virus is strong, the arbitrary protein can be produced efficiently.

It is preferable that the virus vector cDNA that has incorporated the gene that encodes the arbitrary protein, and the ribozyme sequence ligated to the 3' end of the cDNA be placed under the transcriptional control of an inducible promoter. It is therefore preferable that a DNA fragment of the present invention include an inducible promoter. The DNA fragment therefore includes: a virus vector cDNA in which a gene that encodes an arbitrary protein has been inserted downstream of an inducible promoter; and the ribozyme sequence ligated to the 3' end of the cDNA. The inducible promoter suppresses expression in an open system such as a farm field, and induces protein production in a closed system such as a factory. Even a protein that is toxic to plant growth can be produced by inducing production after the plant has grown. The inducible promoter is not particularly limited, and conventional promoters with the foregoing properties can be used as exemplified above. Specific examples of suitable promoters include: chemically induced promoters such as tetracycline, heat-shock promoters, and promoters activated by steroid hormone or estrogen. More specifically, 6XUASga14, 0LexA-46, and GRE are examples of promoters that are capable of inducing transcription with steroid hormone, estrogen, and ecdysone, respectively.

In order to control transcription with the inducible promoter, a transcription factor is needed that is activated by a transcription inducer. As such, a DNA fragment of the present invention requires a gene for encoding a transcription factor that is activated by a transcription inducer. The transcription factor is suitably selected according to the type of promoter used. For example, transcription factor GVG is used when 6XUASga14 is used as the promoter capable of inducing steroid hormone-dependent transcription, and XVE is used when 0LexA-46 is used as the promoter capable of inducing estrogen-dependent transcription. When GRE is used as the promoter capable of inducing ecdysone-dependent transcription, a chimeric protein of ecdysone receptors GR Act and DBD and herpesvirus transactivation domain HecR LBD is used as the transcription factor. It is preferable that a gene that encodes the transcription factor be placed downstream of a promoter commonly used in plants, for example, such as the cauliflower mosaic virus 35S promoter. With the gene placed at such a location, the transcription factor is expressed at all times in an inactivated state. The inactive transcription factor can be activated by treating it with an inducer such as the steroid hormone, with the result that the gene placed downstream of the promoter is transcribed.

A vector according to the present invention includes the DNA fragment as constructed above, and is incorporated in the genome of a cell. By being incorporated in the genome, it is ensured that the genes contained in the vector are passed onto the daughter cells after the cell division, thereby maintaining the efficiency of protein production. The genome is not limited to the chromosomes (nuclear genome), and it may be mitochondrion genome or chloroplast genome. The vector sequence other than the DNA fragment is not particularly limited, and it may be those of conventional vectors that can be incorporated in the genome. An example of vectors that can be incorporated in the genome of a plant cell is the Ti plasmid of *Agrobacterium tumefaciens*.

The method of constructing the DNA fragment and vector is not particularly limited, and conventional genetic engineering techniques can be used.

(F) Plant Cell Transforming Kit

The DNA fragment and vector are useful for the preparation of cells for producing useful arbitrary proteins. Thus, it would be convenient if the DNA fragment and vector were provided as a kit along with reagents and instruments needed for the transformation of cells. This allows a user to easily prepare transformants that include the DNA fragment and vector.

A transforming kit according to the present invention can have any arrangement as long as it includes the DNA fragment and vector. Other than the DNA fragment and vector, the kit may include, for example, cells, culture media, restriction enzymes, modification enzymes, transcription inducing chemicals (steroid hormone, estrogen), culture flasks, and *Agrobacterium* (when plant cells are used).

(G) Transformant and Protein Producing Process

A transformant of the present invention is obtained by transferring the DNA fragment and vector into a plant cell, or by using the plant cell transforming kit. The transformant of the invention allows for production of a target useful protein.

The transformation method is not particularly limited and can be suitably selected according to the type of host cell. In the case where the DNA fragment does not have a unique vector sequence, an electroporation method, a particle gun method, and a calcium phosphate method can be used, for example. A common transformation method used for plant cells is the transformation method using *Agrobacterium* (*Agrobacterium* method). The present invention can suitably use the *Agrobacterium* method. In order to transform the host cell by the *Agrobacterium* method, a Ti plasmid needs to be constructed that includes the DNA fragment of the present invention.

The type of host cell is not particularly limited, and the host cell may be an animal cell or a plant cell. A cell suitable for producing a target protein is suitably selected. The transformants may be cultured cells or living organisms themselves (both plants and animals). In plants, tobacco BY2 cells can be suitably cultured to obtain transformants. Alternatively, a tobacco plant itself may be used. However, these are not the only examples. As mentioned earlier, the tobacco BY2 cell is the most widely cultured plant cell line in the world, and it has a fast growth rate, allows for easy genetic manipulation, and can be cultured in mass quantity.

Novel features of transformants according to the present invention include:

(I) Use of a ribozyme sequence in the cultured transformed cells in which the virus vector is transcribed and expressed;

(II) Use of a ribozyme sequence in transformants (both cultured cells and plants themselves) in which a tobamovirus vector is transcribed and expressed; and (III) Use of a ribozyme sequence in transformants that allow the virus vector to be transcribed and expressed.

Transformed cells according to the present invention constructed by the inventors of the present invention have novel features as described above. Specifically, the inventors constructed BY2 cells that were transformed with a tobamovirus ToMV vector having incorporated a foreign gene, ligated to a ribozyme sequence, and including a DNA fragment downstream of the promoter capable of inducing steroid hormone-dependent transcription. Note that, advantages of using plant culture cells in producing useful proteins, particularly as compared with using plants themselves, are as described in (a) through (k) above.

Another advantage of the system using plant culture cells, as compared with the eukaryotic animal counterpart, is the considerably low cost of medium preparation, which is advantageous for large-scale production.

It has been shown that the RNA plant virus can also replicate in non-plant eukaryotes, such as yeast cells, through intentional inoculation or transformation. The present invention is therefore applicable not only to BY2 and other plant culture cells but also to other eukaryotes in producing inducible virus vector systems.

The present invention also provides a protein producing process using the transformant as described above.

In the following, description is made as to (H) a producing process of a transformant for producing a protein according to the present invention, (I) a transformant for producing a protein according to the present invention, and use of such a transformant, and (J) a kit for producing a transformant for producing a protein according to the present invention.

(H) Producing Process of a Transformant for Producing a Protein according to the Present Invention A producing process of a transformant for producing a protein according to the present invention (hereinafter "transformant producing process") includes: (1) a first transforming step of transfecting a cell with a transcription factor-expressing DNA fragment in which a gene that encodes a transcription factor is ligated to a promoter for expressing the transcription factor; (2) a screening step of screening the transformants, obtained in the first transforming step, for an individual expressing the transcription factor; and (3) a second transforming step of transfecting the transformant, selected in the screening step, with a protein-expressing DNA fragment in which cDNA of a virus vector that has been prepared by inserting a gene that encodes an arbitrary protein into an RNA virus is ligated to a promoter for inducing transcription with the transcription factor. The following will describe each step.

(H-1) First Transforming Step

In the first transforming step, a suitable host cell is transfected with a DNA fragment (transcription factor-expressing DNA fragment) that has been constructed by ligating a gene that encodes a transcription factor to a promoter for expressing the transcription factor (transcription factor-expressing promoter). By the first transforming step, a transformant (cell) is produced (obtained) in which the transcription factor for inducing transcription of a virus vector-expressing promoter (described later) is expressed both stably and efficiently. Specifically, the first transforming step produces (obtains) a potential transformant (cell) in which a gene that encodes the transcription factor has been incorporated at a chromosomal locus suitable for the expression of the transcription factor of the host cell.

In transfecting the host cell with the transcription factor-expressing DNA fragment, it is at present difficult to control the chromosomal location where the DNA fragment is incorporated, as described above. Therefore, the transcription factor-expressing DNA is not always inserted at a chromosomal location suitable for the expression of the transcription factor, even if it successfully transfected the host cell and produced the transformant (cell). As a result, the transformants have different expression levels of the transcription factor. Thus, the first transforming step is intended to stably and efficiently produce (obtain) transformants (cells).

In the following, description is made as to the transcription factor-expressing DNA fragment used in the first transforming step. The transcription factor-expressing DNA fragment includes a transcription factor-coding gene ligated downstream of the promoter for expressing the transcription factor. The transcription factor-expressing DNA fragment may additionally include DNA segments such as a vector sequence, a terminator, and a drug-resistant marker. The transcription factor-expressing DNA fragment can be constructed by an ordinary genetic engineering technique.

The transcription factor-expressing promoter is not particularly limited as long as it can express the transcription factor. Specifically, the transcription factor-expressing promoter may have its promoter activity permanently (hereinafter referred to as "permanent promoter"), or the promoter activity may be induced by the transcription factor. Of these promoters, the former is more preferable because controlling the expression of the transcription factor with another transcription factor is disadvantageous in terms of complexity of the protein expression system and cost, among other things. Examples of permanent promoters include: PG10-90 (see Ishige, F., Takaichi, M., Foster, R., Chua, N. H. and Oeda, K. (1999) A G-box motif SEQ ID NO. 5 (GCCACGTGCC) tetramer confers high-level constitutive expression in dicot and monocot plants. Plant J. 20, 127-133.), a ubiquitin promoter, and an actin promoter.

The transcription factor is not particularly limited and can be suitably selected from those capable of inducting the promoter included in the protein-expressing DNA fragment that is transferred in the second transforming step to be described later. The transcription factors are preferably those activated by a hormone, which may be estrogen, steroid hormone, or ecdysone, for example. Such transcription factors remain inactive in the absence of hormones and cannot activate the promoter. In the presence of hormones, the transcription factors turn active and induces the promoter. Such properties of transcription factors allow for delicate control of target protein production and thereby produce the target protein more safely. That is, where protein production is not needed or needs to be avoided, one only needs not to add hormone to the protein producing system.

The transcription factor activated by hormone is combined with the promoter induced by the transcription factor. Possible combinations include, for example: the combination of GVG, which is a transcription factor activated by steroid hormone, and 6xUASga14, which is a promoter induced by GVG; the combination of LexA-VP16-hER, which is a transcription factor activated by estrogen, and OlexA-46 (Zuo J, Niu Q W, Chua N H. "An estrogen receptor-based transactivator XVE mediates highly inducible gene expression in transgenic plants." Plant J. 2000, 24: 265-273), which is a promoter inducible by LexA-VP16-hER; and the combination of the chimeric protein of ecdysone receptors GR Act and DBD and herpesvirus transactivation domain HecR LBD, which is a transcription factor activated by ecdysone, and GRE, which is a promoter inducible by the chimeric protein transcription factor. In the case where a plant or a plant cell is used as the protein producing host, the combination of transcription factor LexA-VP16-hER and promoter $O_{lexA}$-46 is preferable because, in this case, the hormone used for the activation is least detrimental to the host. Note that, as with the foregoing inducible promoters, conventional inducible promoters may be suitably combined with the transcription factors.

Figure 8:
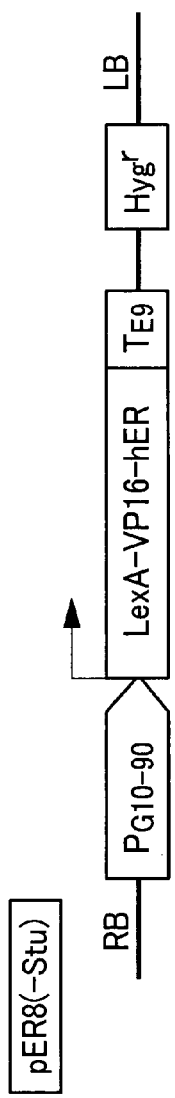
FIG. 8(a) is a schematic view illustrating a structure of transcription factor-expressing DNA fragment introducing vector pER8 (–Stu)
FIG. 8(b) is a schematic view illustrating a structure of protein-expressing DNA fragment introducing vector pBICER8-ToMVerG3 (SF3) SRz.
Figure 8:
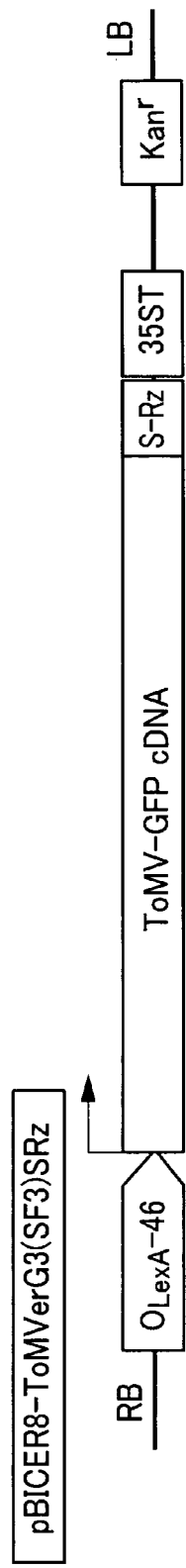

FIG. 8(a) illustrates an example of transcription factor-expressing DNA. In FIG. 8(a), a portion of Ti plasmid pER8 (−Stu) used as a transforming vector is depicted. From the left of the drawing, the vector includes permanent promoter PG10-90 for expressing the transcription factor, fusion transcription factor LexA-VP16-hER containing an estrogen receptor, terminator sequence $T_{E9}$ ligated at the 3' end of LexA-VP16-hER, and hygromycin-resistant gene Hyg" provided as a drug resistant marker.

<Host Cell Transfected with Transcription Factor-Expressing DNA Fragment, and DNA Fragment Transfer Method>

The host cell transfected with the transcription factor-expressing DNA fragment is not particularly limited, and it may be a plant cell or an animal cell. However, plant cells are more preferable than animal cells for reasons that plant cells grow more rapidly and therefore have a lower risk of contamination, and that the cost of culture media is considerably cheaper. As used herein, the "animal cells" and "plant cells" refer to cells, tissues, and organs derived from animals and plants. Of these, (culture) cells that can grow in, for example, a liquid medium is particularly preferable.

Non-limiting examples of animals include: human; monkey; dog; sheep; goat; rabbit; mouse; rat; guinea pig; Chinese hamster; cattle; horse; pig; fishes such as ricefish and zebrafish; silkworm; fall armyworm (*Spodoptera frugiperda*). Non-limiting examples of plants include: rice; mouseear cress (*Arabidopsis thaliana*); barley; wheat; tobacco; tomato; cucumber; soy bean; potato; corn; vinca (*Catharanthus roseus*); mouseear cress (*Arabidopsis thaliana*); and alfalfa. Other than plant and animal cells, bacteria such as *bacillus subtilis* and lactic acid bacteria, or unicellular cells such as yeasts may be used as host cells.

Non-limiting examples of animal cells include: HeLa cell; CHO cell; melanoma cell; and mouse 3T3 cell. Non-limiting examples of plant cells include: tobacco BY-2 cell; potato cell; rice cell; sweet potato cell; soy bean cell; parsley cell; mouseear cress cell; wheat cell; corn cell; and vinca cell.

In the Examples to be described later, the BY-2 tobacco cell is used as a host.

The method by which the transcription factor-expressing DNA fragment is introduced into the host cell is not particularly limited, and a transformation method is suitably selected according to the type of host cell. In the case where the DNA fragment does not have a unique vector sequence, an electroporation method, a particle gun method, and a calcium phosphate method can be used, for example. A common transformation method used for plant cells is the transformation method using *Agrobacterium* (*Agrobacterium* method). The present invention can suitably use the *Agrobacterium* method. In order to transform the host cell by the *Agrobacterium* method, a Ti plasmid needs to be constructed that includes the DNA fragment of the present invention. Other conventional methods suitable in the invention include: a protoplast/spheroplast method; a calcium phosphate method; a liposome method; and a DEAE dextran method, for example.

It is preferable that the transcription factor-expressing DNA fragment be incorporated in the genome of a cell. By being incorporated in the genome, it is ensured that the genes contained in the vector are passed onto the daughter cells after the cell division, thereby maintaining the efficiency of transcription factor (protein) production. The genome is not limited to the chromosomes (nuclear genome), and it may be mitochondrion genome or chloroplast genome.

The method of confirming whether the transcription factor-expressing DNA fragment has been incorporated in the host cell is not limited to a particular method and a variety of conventional methods can be used therefor. Specifically, various markers can be used. For example, a gene lacking in the host cell is used as a marker, and a plasmid or the like containing the marker and the recombinant plant virus gene is introduced as an expression vector into the host cell. Successful transfer of the gene of the present invention can be confirmed by the expression of the marker gene. In the Examples to be described later, a drug-resistant marker (hygromycin-resistant marker Hygr) is used, for example. Candidate strains of transformants are cultured in a hygromycin-containing medium, which then allows for screening of transformants from the cultured cell lines. Other examples of drug-resistant markers that are effective for the screening of plant cells include bialaphos-resistant marker and kanamycin-resistant marker. For the screening of animal cells, the following markers and genes are effective: puromycin-resistant marker, bleomycin-resistant marker, XGPRT gene, DHFR gene, and thymidine kinase-resistant marker. In yeasts, autotrophic markers such as a uracil auxotrophic marker can be used for the screening. The screening method of transformants is not limited and may be suitably selected depending on the type of host transfected with the expression vector. Alternatively, a genomic PCR method may be used in which a total length gene of the transferred protein (transcription factor) is specifically amplified using the genomic DNA of the host cell as a template. With this method, successful transfer of the gene can be conformed if amplification of the gene that encodes a target protein (transcription factor) were confirmed by electrophoresis or the like.

(H-2) Screening Step

The second step of the transformant producing process is the screening step. In the screening step, the transformants (cells) obtained in the first transforming step are screened for an individual in which the transcription factor is expressed both stably and efficiently. In other words, in the screening step, a transformant (cell) is selected in which a gene that encodes the transcription factor has been incorporated at a host cell chromosomal locus suitable for the expression of the transcription factor. The screening method used in the screening step is not limited to a specific method as long as it can screen the transformants (cells), obtained in the first transforming step, for an individual in which the transcription factor is expressed both stably and efficiently.

For example, a Western blotting method, an ELIZA method, or a dot blotting method may be used as the method of expressing the expression protein from the transformants (cells) and detecting its expression level using an antibody against the transcription factor. Further, for example, a Northern blotting method or a dot blotting method may be used as the method of extracting expression RNA from the transformants (cells) and detecting the expression level of the mRNA of the transcription factor using a probe complementary to the genetic sequence of the transcription factor. The expression level of the transcription factor mRNA can also be detected by an RT-PCR method, a realtime PCR method, or a microarray method, for example.

(H-3) Second Transforming Step

In the second transforming step, the transformant (cell) selected out in the screening step with the high-level expression of the transcription factor (hereinafter referred to as "transcription factor-expressing transformant (cell)") is transfected with a protein expressing DNA fragment in which cDNA of a virus vector that has been constructed by inserting a coding gene of an arbitrary protein into an RNA virus is ligated to an inducible promoter induced by the transcription factor expressed in the transcription factor-expressing transformant. In this manner, the transformant that shows high-level expression of the transcription factor is transfected with cDNA of a virus vector that has been constructed by inserting a coding gene of a target protein. This enables the transformant (cell) to produce the target protein more reliably and more efficiently.

<Protein-Expressing DNA Fragment>

The protein-expressing DNA fragment is used to produce an arbitrary protein in the transformant (cell), and it includes: cDNA of a virus vector that has been constructed by inserting a coding gene of an arbitrary protein into an RNA virus; and an inducible promoter induced by the transcription factor expressed in the transcription factor-expressing transformant (cell). The protein expressing DNA fragment may additionally include various types of DNA segments, examples of which include: a cloning site (preferably, multiple cloning site) for inserting a coding gene of an arbitrary protein; a vector sequence; a terminator; and a drug resistant marker. The transcription factor-expressing DNA fragment can be prepared by an ordinary genetic engineering technique.

The inducible promoter is suitably selected according to the type of transcription factor produced by the transcription factor-expressing transformant. For possible combinations of promoters and transcription factors, see the examples in the foregoing section (H-1) concerning the first transforming step.

The type of arbitrary protein produced in the cell is not particularly limited. It may be a useful foreign protein, or a protein that originates in the plant itself. For example, a human protein usable as a medicament is suitable.

The virus vector is not particularly limited as long as it is obtained from an RNA virus. For example, the virus vector may be obtained from a double strand RNA virus, a single strand (−) RNA virus, and a single strand (+) RNA virus. Among these examples, the single strand (+) RNA virus is particularly preferable because the RNA that is transcribed from the cDNA in the cell directly serves as mRNA. Further, since the single strand (+) RNA virus replicate rapidly, the target protein can be produced efficiently.

The virus vector is not limited to those derived from plant viruses, and various types of virus vectors can be used that are derived from various RNA viruses, including animal viruses and phages. For the purpose of producing an arbitrary protein in plant cells, a virus vector derived from a plant virus is preferably used. Particularly, a virus vector derived from a virus having a suppressor against the silencing of the plant is preferable. With the use of the virus vector having the silencing suppressor, there will be no degradation of mRNA in the second half of amplification. Examples of plant viruses having the silencing suppressor were given above.

It is preferable that the ribozyme sequence be ligated to the 3' end of the virus vector cDNA. With the ribozyme sequence, the terminator-derived sequence and the poly-A sequence can be cut that are added to the 3' end of the viral RNA transcribed from the cDNA in the cell and that are detrimental to the replication of the virus. As a result, the replicating ability of the virus does not suffer, and the foreign protein can be produced efficiently. The ribozyme sequence is not particularly limited as long as it can cut the additional sequences ligated to the 3' end of the viral RNA. Examples include the ribozyme sequence of hepatitis delta virus (GenBank accession No. X77627), and the ribozyme sequence of satellite tobacco ringspot virus (GenBank accession No. M17439).

It is preferable that a gene that encodes an arbitrary protein be substituted with the gene that encodes the coat protein of the virus. With the gene inserted at such a site, there will be no production of the viral coat protein, and the amplified viral gene will not form particles and infect other plants, thereby solving the problem of viral spreading.

FIG. 8(b) illustrates an example of a protein expressing DNA fragment. In FIG. 8(b), a portion of Ti plasmid pBICER8-ToMVerG3 (SF3)SRz used as a transforming vector is depicted. From the left of the drawing, the vector includes: promoter OlexA-46 induced by the fusion transcription factor LexA-VP16-hER activated by estrogen; tomato mosaic virus vector ToMV-GFP cDNA having incorporated therein a green fluorescent protein gene (hereinafter "GFP gene") as a reporter gene; a satellite tobacco ringspot virus ribozyme sequence S-Rz ligated to the 3' end of the ToMV-DFP cDNA; 35S terminator sequence 35ST; and kanamycin-resistant gene Kan$^r$ provided as a drug resistant marker. Note that, the protein expressing DNA fragment can be transferred into the transcription factor-expressing transformant according to the procedure described in the foregoing section (H-1) concerning the first transforming step.

As described above, the most significant feature of the transformant (cell) producing process of the present invention is that the transcription factor-expressing DNA fragment and the protein expressing DNA fragment that are used to transfect the host cell are transferred into the host cell on separate vectors. This is different from conventional methods in which the transcription factor-expressing DNA fragment and the protein-expressing DNA fragment are carried on the same vector to transform the host cell. The advantages of the transformant producing process having such a feature are as follows. (i) The expression level of transcription factors that control (affect) the expression of the virus vector and proteins can be maintained constant. Thus, by first producing (obtaining) a transformant (cell) that shows high-level expression of the transcription factor, and then transfecting the transformant with the protein expressing DNA fragment, it is possible to easily obtain transformants (cells) that show high-level expression of the virus vector and target proteins. (ii) The transformants (cells) showing the same expression level for the transcription factors can be transfected with protein-expressing DNA fragments containing various types of virus vectors. This allows for a comparison of expression efficiency or other properties of the virus vectors. In this way, improvements or other changes can easily be made on the virus vectors.

With the transformant (cell) producing process, it is possible to reliably obtain a transformant (cell) in which the coding genes for the transcription factor and the virus vector have been incorporated in the chromosomal loci most suited for their expression.

(I) Protein-Expressing Transformant according to the Present Invention and Use thereof A protein-expressing transformant according to the present invention (hereinafter, "transformant of the invention") is a protein-expressing transformant (cell) produced by the transformant producing process. In the transformant of the invention, the coding genes for the transcription factor and the virus vector are incorporated in the chromosomal loci most suited for their expression. Therefore, with the transformant of the invention, the target protein can be efficiently produced.

A protein producing process according to the present invention (hereinafter, "protein producing process of the invention") uses the transformant of the invention. Specifically, in the protein producing process, the target protein is collected from the transformant of the invention having incorporated therein a coding gene of the target protein. The target protein can be obtained in mass quantity preferably by multiplying the transformants of the invention through culturing, cultivation, breeding, or the like, and collecting the target protein from these transformants. The conditions of culturing, cultivating, or breeding the transformants of the invention are not particularly limited. Suitable conditions can be selected for the transformants of the invention. The type of medium used to culture the plant cells is not particularly limited, and it may optionally contain inorganic salts, carbon source, vitamins, and amino acids. Additionally, the culture medium may be supplemented with coconut milk or yeast extracts to promote growth. Further, plant hormones such as auxin/cytokinin, gibberellin, abscisic acid, and ethylene may be added. Culture conditions such as light, temperature, and the presence or absence of ventilation can be suitably set according to the type of cultured cells. For example, in using tobacco BY2 cells, MS medium containing 370 mg/l of potassium dihydrogen phosphate, 1 mg/l of thiamine hydrochloride, 3% sucrose, and 0.2 mg/l of 2,4-D may be used, and the cells may be sub-cultured (1/100) every week in dark at 26° C. using a rotary incubator (135 revolutions per minute).

The transformants of the invention are not particularly limited, and may be animals and plants themselves, or plant and animal cells. However, in order to quickly produce a large amount of protein, it is preferable that the transformants be (culture) cells. Further, plant culture cells are more preferable for reasons that the cells are easy to handle and the cost of culture media is considerably cheaper. As an example of plant culture cells, tobacco BY2 cells are may be used. Note that, advantages of using plant culture cells in producing useful proteins, particularly as compared with using plants themselves, are as described in (a) through (k) above.

(J) Producing Kit of Protein-Producing Transformant according to the Present Invention A producing kit of a protein-producing transformant according to the present invention (hereinafter referred to as "present kit") is a kit for performing the transformant producing process. The arrangement of the present kit is not particularly limited. Preferably, the present kit includes: a transcription factor-expressing DNA fragment in which a coding gene of a transcription factor is ligated to a promoter for expressing the transcription factor; and/or a protein-expressing DNA fragment in which cDNA of a virus vector that has been constructed by inserting a coding gene of an arbitrary protein into an RNA virus is ligated to an inducible promoter which is induced by the transcription factor. Specifically, the present kit may include, for example, pER8 (-Stu), which is a transcription factor-expressing DNA fragment, and/or pBICER8-ToMVerG3 (SF3)SRz, which is a protein-expressing DNA fragment.

A user of the present kit can obtain the protein-producing transformant through the steps of (a) transferring a transcription factor-expressing DNA fragment into a suitable host, (b) screening the transformants for an individual showing high-level expression of the transcription factor, and (c) transfecting the transformant with a protein expressing DNA fragment that has incorporated a coding gene of the target protein. Note that, a coding gene of the target protein can be inserted into the transcription factor-expressing DNA fragment of the present kit by a genetic engineering technique.

It is more preferable that the present kit include the transcription factor-expressing transformant and/or protein-expressing DNA fragment. Specifically, the kit may include, for example, transcription factor-expressing tobacco BY2 cell ER8-20, which is a transcription factor-expressing transformant, and pBICER8-ToMVerG3 (SF3)SRz, which is a protein-expressing DNA fragment, both of which were obtained in the Examples to be described later.

Because the transcription factor-expressing transformant is already provided, a user of the present kit only needs to perform the step (c), and can obtain the protein-producing transformant more quickly and more conveniently.

The present kit may additionally include, for example, cells, culture media, restriction enzymes, modification enzymes, transcription inducers (steroid hormone, estrogen, etc.), culture flask, and *Agrobacterium*.

EXAMPLES

The following will describe the present invention in more detail based on Examples and FIGS. 1 through 4. It should be noted that the present invention is not limited in any way by the following description.

Example 1

Steroid Hormone-Induced Protein Expression in Tobacco BY-2 Cells

<Construction of Expression Vector pTA7001-ToMV-erG3(SF3)>

As a virus vector, the ToMV variant (ToMV-erG3(SF3)) was used in which the coat protein gene has been replaced with the GFP gene. The ToMV-erG3(SF3) was kindly provided by Dr. Tetsuo MESHI of the graduate school of Kyoto University.

As a transformation vector, Ti plasmid pTA7001 (Stu) was used that includes a transcription factor (GVG), and a promoter which is induced by steroid hormone. The vector was constructed by inserting StuI site at the transcription origin of pTA7001, using PCR. Note that, pTA7001 was kindly provided by Dr. Chua (Laboratory of Plant Molecular Biology, the Rockefeller University).

Next, cDNA of ToMV-erG3(SF3) was inserted in pTA7001 (Stu), downstream of the promoter which is induced by steroid hormone, so as to construct an expression vector pTA7001-ToMV-erG3(SF3). More specifically, the vector was constructed in the following manner. First, using piL-.erG3(SF3) (see Atsushi Tamai and Tetsuo Meshi, "Tobamoviral movement protein transiently expressed in a single epidermal cell functions beyond multiple plasmodesmata and spreads multicellularly in an infection-coupled manner" Molecular Plant-Microbe interaction (2001) 14: 126-134), the MluI site was replaced with AvrII site with the use of a linker, so as to prepare piL.erG3(SF3) (Avr). Then, using piL.erG3(SF3) as a template, a DNA fragment of about 1600 base pairs at the 5' end of ToMV cDNA that has incorporated SnaBI site at the 5' end by PCR was excised with SnaBI and SpeI. A resulting DNA fragment of about 1220 base pairs was then inserted between the StuI site and SpeI site of pTA7001 (Stu), so as to obtain plasmid pTA7001-ToMV5'-Spe. The plasmid pTA7001-ToMV5'-Spe was then cut at SpeI and AvrII, and a fragment of about 5200 base pair containing the 3' end portion of the cDNA of ToMV variant was inserted at the SpeI site of pTA7001-ToMV5'-Spe, so as to obtain the expression vector pTA7001-ToMV-erG3(SF3).

FIG. 1 illustrates the piL.erG3(SF3).

<Transformation of Tobacco BY-2 Cells>

The expression vector pTA7001-ToMV-erG3(SF3) was transferred into tobacco BY-2 cells by the *Agrobacterium* method. Specifically, the vector was transferred according to the following procedure.

The expression vector was then transferred into the *Agrobacterium tumefacience* EHA105 line by an electroporation method. The resulting cells were pre-cultured in AB sucrose medium containing kanamycin (50 mg/l). The cells were then mixed with tobacco BY-2 cells and placed in a Petri dish, where the cells were allowed to stand for 42 to 48 hours in dark at 26° C. so as to transform the tobacco BY-2 cells. The tobacco BY-2 cells were then washed and spread over a solid medium containing carbenicillin (100 mg/l) and hygromycin (20 mg/l), so as to grow the tobacco BY-2 cells.

The transformed tobacco BY-2 cells were subjected to a steroid hormone treatment (hereinafter may be referred to as "DEX treatment") so as to induce transcription. Specifically, the transformed tobacco BY-2 cells in a liquid medium were supplemented with 30 μM steroid hormone (dexamethasone).

The result of transcription induction was confirmed by observing GFP fluorescence 48 hours after the start of reaction, using a stereo fluorescent microscope (OLYMPUS CORPORATION). In addition, by the TRISOL method, the total RNA 48 hours after the start of induction was extracted for Northern analysis. For the Northern analysis, an RNA probe was used that is complementary to a non-coding region of about 200 bases at the 3' end of ToMV. For the labeling of the probe, the DIG RNA Labeling Kit (Roche Diagnostics) was used. Detection was made with the DIG Luminescent Detection Kit and CDP-Star ® (1,2-dioxetane compound, Roche Diagnostics) according to the manuals provided in the kit.

Figure 2:
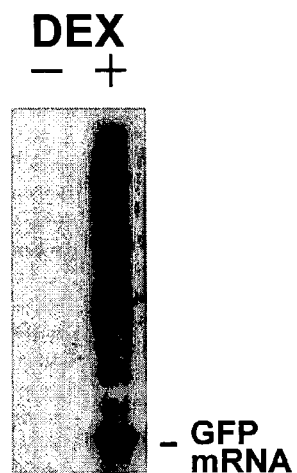
FIG. 2 is a view showing a result of Northern analysis, which was performed in Example to examine transcription of GFP gene mRNA in the presence and absence of a steroid hormone treatment (DEX treatment) in the transformed tobacco BY-2 cells which have incorporated the expression vector pTA7001-ToMV-erG3(SF3).

FIG. 2 shows a result of Northern analysis, which was performed to examine transcription of GFP gene mRNA in the presence and absence of the DEX treatment. As is clear from FIG. 2, the DEX treatment induced transcription of GFP gene mRNA.

Figure 3:
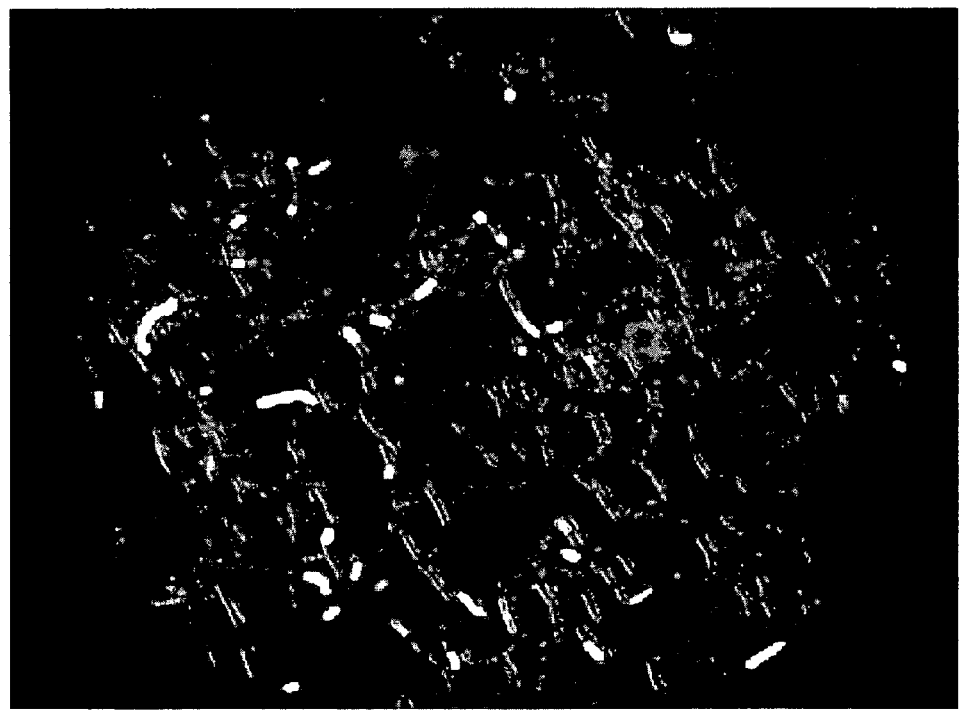
FIG. 3 is a view showing a result of fluorescent microscopy performed in Example, detecting GFP expression of the transformed tobacco BY-2 cells treated with steroid hormone (DEX).

FIG. 3 shows a result of fluorescent microscopy on the transformed tobacco BY-2 cells treated with DEX. As shown in FIG. 3, induced expression of GFP was confirmed by detecting GFP fluorescence.

<Assessment of Pre-Culture Conditions of Tobacco BY-2 Cells>

Assessment was made on pre-culture periods (in days) of a subculture before it is subjected to the DEX treatment, and the expression rate of GFP. The assessment was made according to the following procedure.

The transformed cells were subcultured (1/100) for 3 days, 5 days, and 7 days to provide pre-cultures. Each pre-culture was supplemented with 30 μM steroid hormone (dexamethasone), and was cultured for 48 hours. The cells were observed under an erecting fluorescent microscope (Nikon). Then, the number of cells that showed GFP fluorescence and did not show GFP fluorescence was counted, and the expression rate was calculated from the results.

Figure 4:
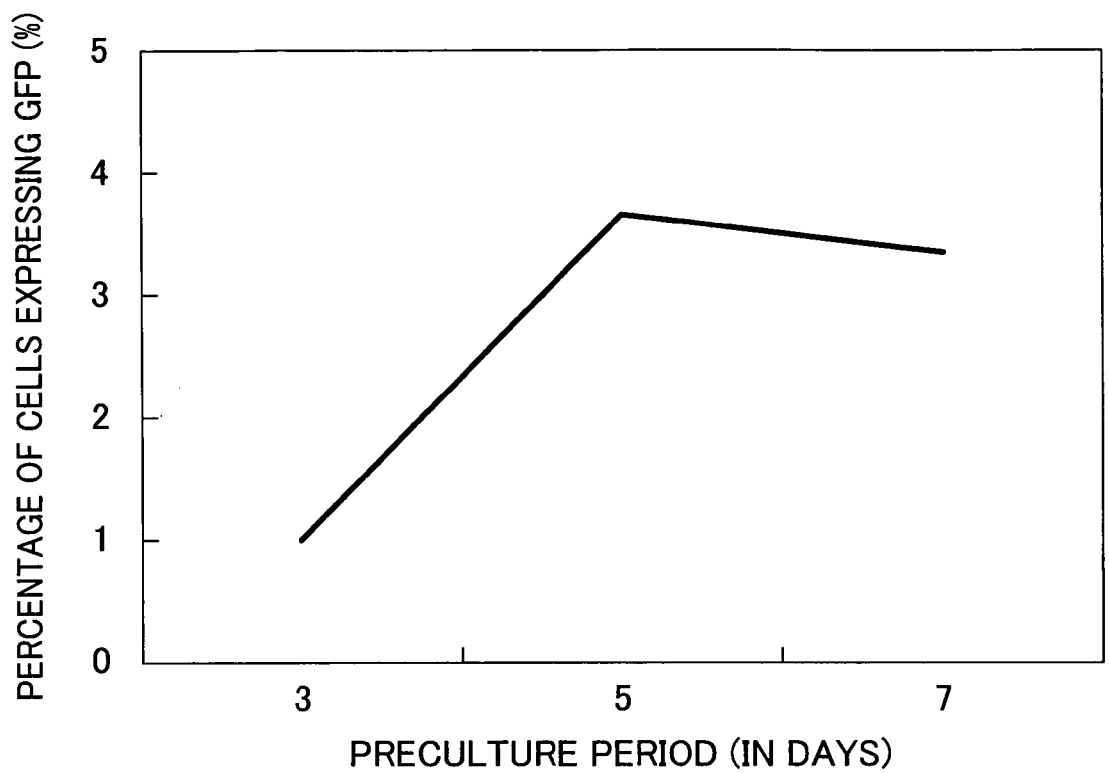
FIG. 4 is a line chart representing a relationship between pre-culture period (3, 5, and 7 days), prior to the DEX treatment of the sub-culture, and GFP expression rate.

FIG. 4 represents a relationship between pre-culture period (in days) and GFP expression rate. The expression rate of GFP was the highest at about 4% in the 5-day pre-culture. This was considered to be due to changes in the physiological conditions of the cells brought about by the cell growth, and such changes influencing the viral sequence replication and GFP expression.

As described above, successful viral RNA amplification and successful induction of GFP expression were observed by the steroid hormone-dependent induction of transcription in the transformed tobacco BY-2 cells having incorporated therein an expression vector that was constructed by transferring cDNA of a recombinant ToMV, in which the coat protein gene has been replaced with GFP gene, into the downstream side of a promoter capable of inducing steroid hormone-dependent transcription. Thus, with the transformed cells, protein producing method, and protein producing kit according to the present invention, proteins can be produced on a large scale and with good efficiency. The product proteins are also safe to use.

The following Examples will describe DNA fragments according to the present invention.

Example 2

[Vector]

Figure 6:
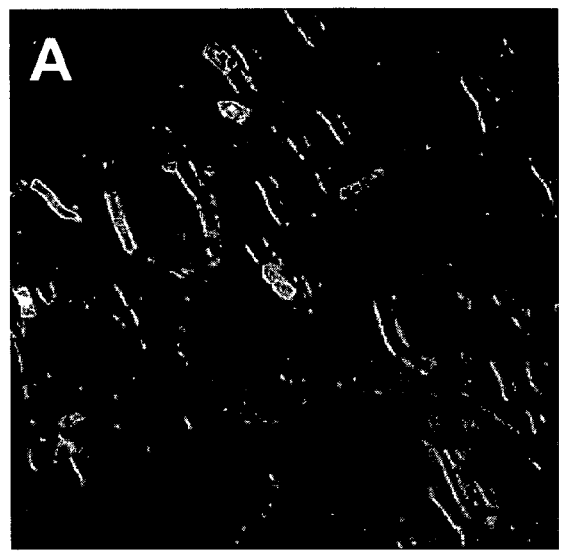
Figure 6:
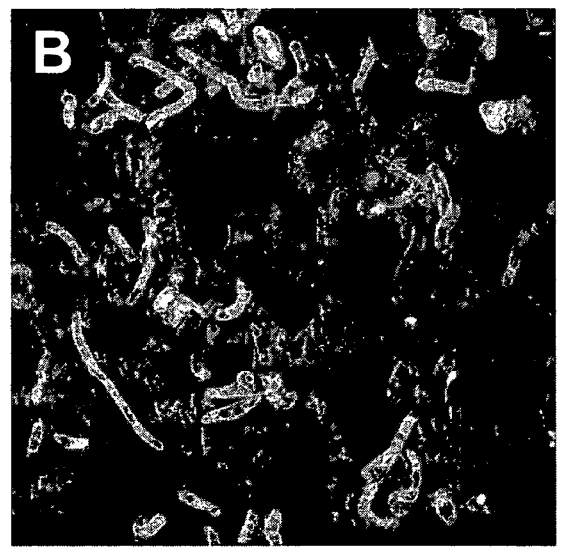
Figure 6:
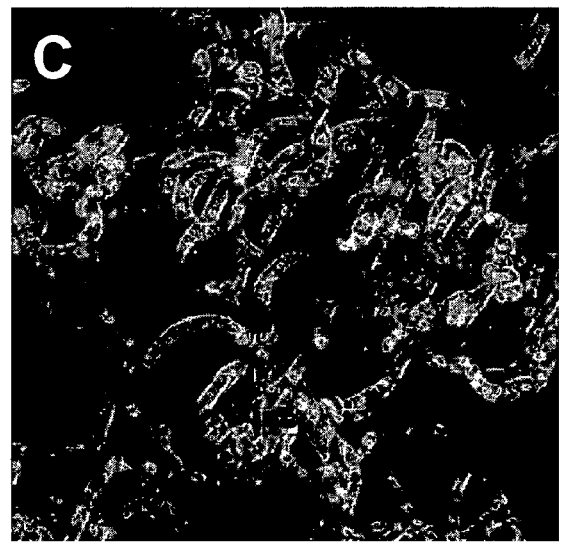

In this Example, a green fluorescent protein (hereinafter "GFP") was used as the protein to be expressed, and a vector was used that contained a ToMV vector having incorporated therein a gene that encodes GFP (hereinafter referred to as "GFP gene"). FIG. 5(A) schematizes a vector to which a ribozyme sequence of hepatitis delta virus has been added. FIG. 5(B) schematizes a vector to which a ribozyme sequence of satellite tobacco ringspot virus has been added. The ribozyme sequence (DNA sequence) used to construct the vector is represented by SEQ ID NO: 1 for the hepatitis delta virus, and by SEQ ID NO: 2 for the satellite tobacco ringspot virus. The sequence represented by SEQ ID NO: 1 was obtained by modifying the anti-genomic ribozyme sequence of a hepatitis delta virus genomic sequence (Gen Bank accession No. X77627, etc.). The sequence represented by SEQ ID NO: 2 was obtained by modifying the ribozyme sequence of a satellite tobacco ringspot virus genomic sequence (GenBank accession No. M17439). In both vectors, the ribozyme sequence was ligated to the 3' end of ToMV vector cDNA. Other than the ribozyme sequences, the two vectors had the same construction. In FIG. 5(A), H-Rz is the ribozyme sequence of the hepatitis delta virus. In FIG. 5(B), S-Rz is the ribozyme sequence of the satellite tobacco ringspot virus. In FIGS. 5(A) and 5(B), 6XUASga14 is the promoter which is induced by steroid hormone, ToMV-GFP cDNA is the cDNA of the tomato mosaic virus having incorporated the GFP gene, 3A is the pea rbcS-3A polyadenylated sequence, Hygr is the hygromycin-resistant gene, E9 is the pea rbc-E9 polyadenylated sequence, GVG is the transcription factor activated by steroid hormone, P35S is the cauliflower mosaic virus 35S promoter, and the scissors indicates the incision site acted upon by the ribozyme.

As the ToMV-GFP cDNA of the vector, cDNA of a ToMV variant in which the ToMV coat protein gene has been replaced with the GFP gene was used. Since the ToMV variant has the mutation in 30 k protein, it is not capable of intercellular movement. As a transformation vector, Ti plasmid pTA7001 (Stu) was used that includes a transcription factor (GVG), and a promoter (6XUASga14) which is induced by steroid hormone. (The Ti plasmid pTA7001 was kindly provided by Dr. Chua, the Laboratory of Plant Molecular Biology, The Rockefeller University.) The vectors shown in FIGS. 5(A) and 5(B) were constructed by inserting cDNA of the ToMV variant into the downstream of the 6XUASga14 promoter of pTA7001 (Stu), and then inserting the ribozyme sequence at the 3' end of the ToMV variant cDNA.

The base sequence (SEQ ID NO: 3) shown in FIG. 5(A) is part of RNA transcribed from the binding gene of ToMV-DFP cDNA and H-Rz (6 bases at the 3' end of ToMV-GFP cDNA, and 18 bases at the 5' end of H-Rz). In the ribozyme sequence of hepatitis delta virus, it is conceivable that incision is made at the 3' end of the viral RNA transcribed from the ToMV-GFP cDNA, as shown by scissors in FIG. 5(A), and that no additional sequence is attached. The base sequence (SEQ ID NO: 4) shown in FIG. 5(B) is part of RNA transcribed from the binding gene of ToMV-DFP cDNA and S-Rz (6 bases at the 3' end of ToMV-GFP cDNA, and 15 bases at the 5' end of S-Rz). In the ribozyme sequence of satellite tobacco ringspot virus, it is conceivable that incision is made with the additional 3 bases (guc) attached to the 3' end of the viral RNA transcribed from the ToMV-GFP cDNA, as shown by scissors in FIG. 5(B).

Note that, a vector without the ribozyme sequence was used as a control vector (a vector lacking H-Rz in FIG. 5(A), or a vector lacking S-Rz in FIG. 5(B)).

[Experiment Methods]

The vector shown in FIG. 5(A) and the vector shown in FIG. 5(B) were transferred into tobacco BY2 cells by the *Agrobacterium* method. Specifically, the vector shown in FIG. 5(A) and the vector shown FIG. 5(B) were separately transferred into the *Agrobacterium tumefacience* EHA105 line by the electroporation method. The resulting cells were pre-cultured in AB sucrose medium containing kanamycin (50 mg/l). The cells were then mixed with BY2 cells and placed in a Petri dish, where the cells were allowed to stand for 42 to 48 hours in dark at 26° C. so as to transform the BY2 cells. The BY2 cells were then washed and spread over a solid medium containing carbenicillin (100 mg/l) and hygromycin (20 mg/l), so as to grow the BY2 cells. As a result, about 100 antibiotic-resistant calluses (transformed calluses) were obtained. In the same manner, the control vector was transferred into BY2 cells, and about 50 transformed calluses were obtained. The resulting calluses were cultured in a liquid medium to obtain transformed BY2 cells. The BY2 cells were cultured in MS medium containing 370 mg/l of potassium dihydrogen phosphate, 1 mg/l of thiamine hydrochloride, 3% sucrose, and 0.2 mg/l of 2,4-D. The cells were cultured in dark at 26° C. using a rotary incubator (135 revolutions per minute), and a sub-culture (1/100) was made every week. Transcription was induced by adding a stationary phase cell culture (1/20) to a liquid medium containing 30 μM dexamethasone. After 48 hours, GFP-specific fluorescence was observed with a stereo fluorescent microscope (OLYMPUS CORPORATION) and an erecting fluorescent microscope (NIKON). Then, the number of cells that showed GFP fluorescence and did not show GFP fluorescence was counted, and the expression rate was calculated from the results.

[Results]

FIG. 6(A) through FIG. 6(C) show observed images of induced GFP expression in the transformed BY2 cells. FIG. 6(A) represents BY2 cells transformed with the control vector to which no ribozyme sequence was added. FIG. 6(B) represents BY2 cells transformed with the vector to which the ribozyme sequence of the hepatitis delta virus was added. FIG. 6(C) represents BY2 cells transformed with the vector to which the ribozyme sequence of the satellite tobacco ringspot virus was added. As is clear from FIG. 6(A) through FIG. 6(C), the number of cells expressing GFP is considerably greater in FIGS. 6(B) and 6(C) than in FIG. 6(A).

Figure 7:
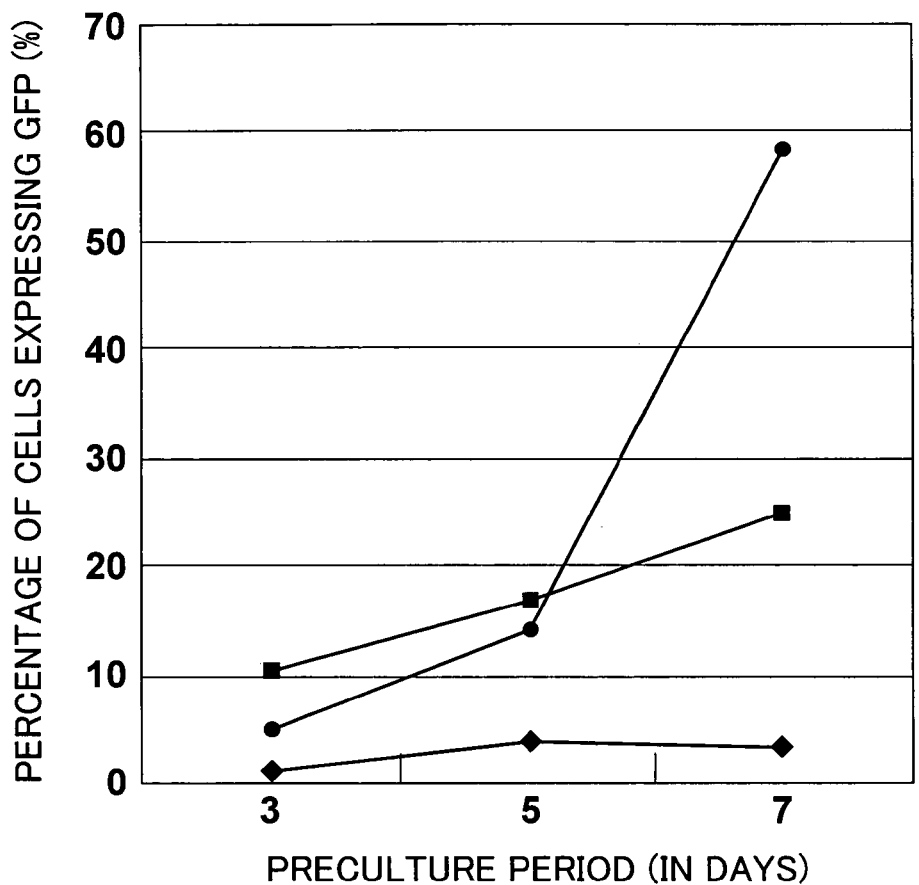
FIG. 7 represents percentages of cells expressing GFP, in regard to BY2 cells transformed with the control vector, BY2 cells transformed with the ribozyme sequence of hepatitis delta virus, and BY2 cells transformed with the ribozyme sequence of satellite tobacco ringspot virus.

FIG. 7 represents percentages of BY2 cells expressing GFP. The notations used in FIG. 7 are as follows. Solid diamond: BY2 cells transformed with the control vector; Solid square: BY2 cells transformed with the ribozyme sequence of hepatitis delta virus; Solid circle: BY2 cells transformed with the ribozyme sequence of satellite tobacco ringspot virus. As used herein, the "PRECULTURE PERIOD (IN DAYS)" means the number of days the cells were sub-cultured prior to the steroid hormone treatment. As in clear from FIG. 7, with the control vector, the percentage of GFP-expressing cells was below 5% even on day 7. On the contrary, the percentage of GFP-expressing cells was about 25% in the vector containing the ribozyme sequence of hepatitis delta virus, and about 60% in the vector containing the ribozyme sequence of satellite tobacco ringspot virus.

The experiment therefore showed that addition of the ribozyme sequences greatly increases the percentage of GFP-expressing cells.

In the following, description is made as to a producing process of a protein-expressing transformant, and a protein-producing transformant produced by the producing process.

Example 3

Production of GFP-Producing Transformed Tobacco BY2 Cells

[Construction of a Transcription Factor-Expressing DNA Fragment Transfer Vector]

Ti plasmid pER8 (−Stu) was used as the vector for transferring the transcription factor-expressing DNA fragment into a host cell (tobacco BY2 cell) ("transcription factor-expressing DNA fragment transfer vector"). The Ti plasmid pER8 (−Stu) is constructed to include: permanent promoter $P_{G10-90}$; a gene that encodes fusion transcription factor LexA-VP16-hER containing an estrogen receptor; terminator TE9; and hygromycin-resistant gene (Hyg$^r$) provided as a drug resistant marker. FIG. 8(a) schematizes the construction of Ti plasmid pER8 (−Stu).

[Construction of Protein-Expressing DNA Fragment Transfer Vector]

ToMV variant was used in which the coding gene of ToMV coat protein has been replaced with a gene that encodes GFP (hereinafter referred to as "GFP gene"). As the transformation vector, a Ti plasmid was used that includes a promoter $O_{LexA}$-46 capable of inducing steroid hormone-dependent transcription.

In order to transfer a protein-expressing DNA fragment into a host cell (tobacco BY2 cell), a vector pBICER8-ToMVerG3 (SF3)SRz was constructed that includes: ToMV variant cDNA ligated downstream of $O_{LexA}$-46; a satellite tobacco ringspot virus ribozyme sequence S-Rz ligated to the 3' end of the ToMV cDNA; 35S terminator (35ST); and kanamycin-resistant gene Kan$^r$.

FIG. 8(b) schematizes the construction of vector pBICER8-ToMVerG3 (SF3)SRz.

[First Transforming Step: Transferring Transcription Factor-Expressing DNA Fragment into a Host Cell]

The transcription factor-expressing DNA fragment transfer vector pER8 (−Stu) was transferred into tobacco BY2 cells by the *Agrobacterium* method. Specifically, pER8 (−Stu) was transferred into the *Agrobacterium tumefacience* EHA105 line by the electroporation method. The resulting cells were pre-cultured in AB sucrose medium containing kanamycin (50 mg/l). The cells were then mixed with tobacco BY2 cells and placed in a Petri dish, where the cells were allowed to stand for 42 to 48 hours in dark at 26° C. so as to transform the tobacco BY2 cells. The tobacco BY2 cells were then washed and spread over a solid medium containing carbenicillin (100 mg/l) and hygromycin (20 mg/l), so as to grow the transformed tobacco BY2 cells ER8.

[Screening Step: Screening Transcription Factor-Expressing Transformants]

From among the resulting transformed tobacco BY2 cells ER8, 26 cell lines were subjected to the Northern blotting method, so as to select out 3 cell lines showing high-level expression of the transcription factor. As used herein, the term "cell line" refers to a cell population obtained from each colony formed by the cultured transformed cells.

[Second Transforming Step: Transfer of Protein-Expressing DNA Fragment]

Each of the three transcription factor-expressing tobacco BY2 cell lines (ER8-17, ER8-20, ER8-32) were transfected with virus vector pBICER8-ToMVerG3 (SF3) SRz by the *Agrobacterium* method. As a result, transformed cells were obtained.

[Induced Expression of GFP]

The transformed cells of each cell line were sub-cultured (1/100), and cells that were precultured for 7 days from the end of sub-culturing were transferred (1/20) to a medium that has been supplemented with estrogen (the final concentration of 0.01 mM). The cells were cultured for 48 hours and were observed with a stereo fluorescent microscope (OLYMPUS CORPORATION) and an erecting fluorescent microscope (NIKON).

In each cell line, the number of cells that showed GFP fluorescence and did not show GFP fluorescence was counted, and the expression rate was calculated from the results. The cell line that showed GFP fluorescence in more than 1% of cells was taken as GFP high-expression cell line.

Table 1 represents percentages of GFP high-expression cell lines in the transformed cells obtained in each transcription factor-expressing tobacco BY2 cell line. Note that, FIG. 1 shows results only for ER8-17, ER8-20, and ER8-32.

TABLE 1

|   | NUMBER OF CELL LINES WITH HIGH-LEVEL GFP EXPRESSION | TOTAL NUMBER OF CELL LINES | PERCENTAGE OF CELL LINES WITH HIGH-LEVEL GFP EXPRESSION |
|---|---|---|---|
| ER8-20 | 33 | 99 | 33% |
| ER8-17 | 4 | 46 | 9% |
| ER8-32 | 0 | 8 | 0% |

As a result, the percentage of GFP high-expression cell line was the highest at 33% in the transcription factor-expressing tobacco BY2 cell line ER8-20.

Further, each transcription factor-expressing tobacco BY2 cell line was transfected with a protein-expressing DNA fragment in which a fusion protein with GPF appended with MPT (movement protein tag) was used as a target protein. Percentages of GFP high-level expression cell lines were also obtained in the manner described above.

The results are shown in Table 2. Note that, Table 2 shows results only for ER8-20 and ER8-17.

TABLE 2

|   | NUMBER OF CELL LINES WITH HIGH-LEVEL GFP EXPRESSION | TOTAL NUMBER OF CELL LINES | PERCENTAGE OF CELL LINES WITH HIGH-LEVEL GFP EXPRESSION |
|---|---|---|---|
| ER8-20 | 48 | 148 | 32% |
| ER8-17 | 0 | 58 | 0% |

As in the foregoing experiment, the percentage of GFP high-level expression cell line was the highest at 32% in ER8-20. It was therefore found that transformed cells that show high-level expression of a target protein can be obtained with good probability if the transcription factor-expressing tobacco BY2 cell line ER8-20 were transfected with a protein-expressing DNA fragment. Further, since the same result was obtained even with a different target protein, it is conceivable that transformed cells that show high-level expression of target protein can also be obtained with good probability even when the transcription factor-expressing tobacco BY2 cell line ER8-20 were transfected with an expression DNA fragment that has incorporated coding genes of various types of proteins.

Example 4

Estrogen-Dependent Induced Expression of GFP Using GFP-Producing Transformed Tobacco BY2 Cells An attempt was made to induce GFP expression with estrogen, using the GFP high-level expression cells (E113 line) obtained in Example 3 by transforming the transcription factor-expressing tobacco BY2 cell line ER8-20.

[Methods]

The E113 line was sub-cultured (1/100) so as to prepare a preculture on day 0, 1, 2, 3, 4, 5, and 6 of the sub-culture. Each preculture of E113 line was then supplemented with estrogen to the final concentration of 0.01 mM, so as to induce GFP expression.

Then, total RNA was extracted from the E113 line 48 hours after the addition of estrogen, and RNA specific to ToMV was detected by Northern blotting. For the analysis, an RNA probe was used that is complementary to a non-coding region of about 200 bases at the 3' end of ToMV. For the labeling of the probe, the DIG RNA Labeling Kit (Roche Diagnostics) was used. Detection was made with the DIG Luminescent Detection Kit and CDP-Star ® (1,2-dioxetane compound, Roche Diagnostics) according to the manuals provided in the kit.

Total protein was extracted from the E113 line 48 hours after the addition of estrogen, and GFP was detected by Western blotting. The protein (5 μg) was loaded in each lane, and signals were detected with GFP-specific antibody. As to other procedures, the standard procedures of Western blotting were followed.

[Results]

Figure 9:
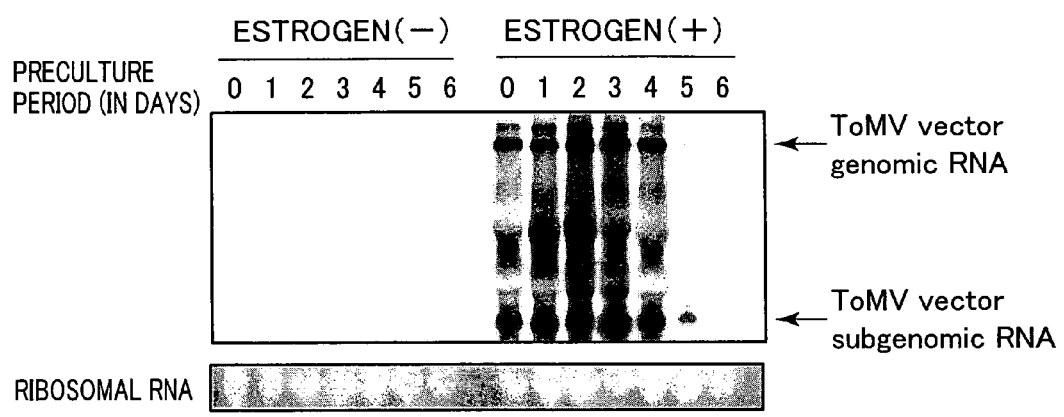
FIG. 9(a) is a photographic view showing results of Northern blotting performed in Example 2, detecting ToMV-specific RNA transcription induced by estrogen.
FIG. 9(b) is a photographic view showing results of Western blotting performed in Example 2, detecting GFP expression induced by estrogen.
Figure 9:
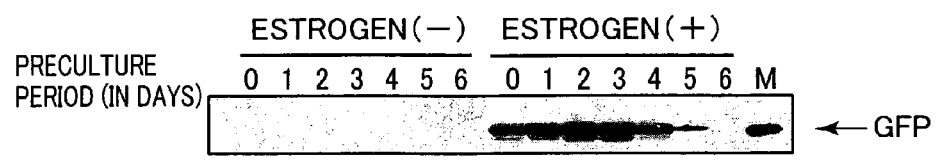

FIG. 9(a) shows results of Northern blotting detecting ToMV-specific RNA. From the left of the drawing, the first 7 lanes represent results of detection in which estrogen-dependent transcription was not induced (estrogen (−)), and the remaining 7 lanes represent results of detection in which estrogen-dependent transcription was induced (estrogen (+)). The results shown in FIG. 9(a) confirmed successful ToMV transcription induced by estrogen. Specifically, ToMV-specific genomic DNA and sub-genomic GFP mRNA were detected from the pre-cultures obtained in day 0, 1, 2, 3, and 4 of the sub-culture. Note that, a lower part of FIG. 9(a) shows detection results of ribosome RNA, confirming that there is no difference in the amounts of ribosome RNA.

FIG. 9(b) shows results of Western blotting detecting GFP. From the left of the drawing, the first 7 lanes represent results of detection in which estrogen-dependent transcription was not induced (estrogen (−)), and the remaining 7 lanes represent results of detection in which estrogen-dependent transcription was induced (estrogen (+)). Further, in FIG. 9(b), the right most lane is a marker, for which 50 ng of refined GFP. The results shown in FIG. 9(b) confirmed successful GFP transcription induced by estrogen. Specifically, a strong GFP signal was detected from the pre-cultures obtained in day 0, 1, 2, 3, and 4 of the sub-culture. The result overlaps the detection result of ToMV-specific RNA shown in FIG. 9(a), suggesting that the ToMV vector is not so mush as means for transferring genes but for multiplying ToMV vector and amplifying eRNA. More specifically, it is envisaged that the expression and replication of ToMV vector RNA, and accompanying increase in the expression level of sub-genomic GFP mRNA shown in FIG. 9(a) are reflected in the expression level of GFP shown in FIG. 9(b).

As described above, the transcription factor-expressing transformant (tobacco BY2 cells) are acquired (produced) in the first transforming step and screening step, and the resulting transcription factor-expressing transformant is transfected with a protein-producing DNA fragment in the second transforming step. In this way, a protein-producing transformant can be efficiently (reliably) is produced (obtained) that can efficiently induce transcription of the virus vector and therefore efficiently produce the target protein. As set forth above, the present invention provides a producing process of a protein-producing transformant, a protein-producing transformant, a protein-producing process, and a kit for producing a transformant for protein production, all of which can greatly reduce the time, cost, and labor required for producing a protein-producing transformant capable of efficiently inducing expression of the virus vector, with the result that useful protein can be produced more efficiently.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

Industrial Applicability

As described above, a transformant according to the present invention is a transformed cell constructed from a naturally occurring cell that has incorporated an expression vector which includes: a gene of a plant virus having (i) a coding gene of a protein to be expressed, and (ii) a suppressor against a virus resistant reaction; and a promoter, capable of inducing hormone-dependent transcription, ligated to the plant virus gene.

A protein producing process according to the present invention uses a transformed cell according to the present invention, and preferably includes a cell culturing step, and a transcription inducing step using hormone.

A protein producing kit according to the present invention is used to perform a protein producing process according to the present invention, and preferably includes the expression vector, a hormone for inducing transcription, and a host cell into which the expression vector is introduced.

With this arrangement, the mRNA of the gene that encodes the target protein can be amplified at high level by the strong replicating ability of the virus. Since the mRNA is amplified with the virus having a suppressor against the virus resistant reaction, degradation of mRNA by the virus resistant reaction of the host cell can be suppressed. This enables the target protein to be produced at high level for sustained time periods. Further, since the host in which the expression vector is introduced is not an individual living organism but a naturally occurring cell, a liquid medium can be used to culture the host. Further, since the host is a cell, the host can be cultured on a large scale, both inexpensively and conveniently. Further, the transformed cell is safe to use because it cannot multiply by itself and dies off even if it leaked out of the system.

Thus, the transformed cell, the protein producing process, and the protein producing kit according to the present invention can efficiently produce protein on a large scale, and are effective in producing proteins that are safe to use.

Thus, with the present invention, protein can be produced in a large amount and at low cost. Product proteins can be effectively used in a wide variety of fields, including pharmaceutical industry, chemical industry, and food industry, for example. Further, since the constituents of the present invention such as a host cell, or an expression vector transferred into a transformed cell of the invention can be commercially marketed as protein-producing kits, the present invention is also applicable to chemical industries providing reagents for experimental and research purposes.

A DNA fragment of the present invention includes cDNA of a virus vector that has incorporated a coding gene of an arbitrary protein, and a ribozyme sequence ligated to the 3' end of the virus vector cDNA. With the ribozyme, it is possible to cut the terminator-derived sequence and the poly-A sequence attached to the 3' end of the viral RNA transcribed from the cDNA in the cell. This greatly increases the amount of viral RNA produced.

Further, since a virus vector is used that originates in a plant virus having a suppressor against the silencing reaction of plants, degradation of mRNA that occurs in the second half of amplification can be suppressed.

Thus, with a DNA fragment, a vector, a transformant, and a protein producing process according to the present invention, a protein synthesis system can be provided by which an arbitrary useful protein can be efficiently and safely produced in plants on a large scale.

A plant transforming kit according to the present invention includes a vector according to the present invention. With the plant transforming kit, a plant capable of producing an arbitrary useful protein can be conveniently produced.

Thus, a plant transforming kit according to the present invention is applicable to various industries, including pharmaceutical and food industries, depending on intended use of the product useful protein.

With a process for producing a transformant for protein production according to the present invention, it is possible to screen for a transformant (cell) that has incorporated a coding gene of the transcription factor on the chromosomal locus most suited for the expression of the transcription factor, i.e., a transformant (cell) that can stably and efficiently express the transcription factor. If such a transformant (cell) were transfected with a virus vector gene, then it would be possible to reliably obtain a transformant (cell) in which a coding gene of the transcription factor and the coding gene of the virus vector are respectively incorporated in chromosomal loci most suited for their expression. As a result, a transformant (cell) that can efficiently produce the target protein can be obtained with less labor and less time.

Further, with a transformant (cell) and a protein producing process according to the present invention, high-level production of a target protein is possible.

Further, with a producing kit of a transformant for protein production, a transformant (cell) that can efficiently and conveniently produce the target protein can be obtained with less labor and less time.

The present invention therefore enables mass production of useful proteins efficiently, inexpensively, and safely. Product proteins can be effectively used in a wide variety of fields, including chemical and food industries. Further, with the present invention, the vector introduced in a transformant of the present invention, as well as a host cell, etc., can be commercially marketed as a protein producing kit. The invention is therefore applicable to chemical industries providing reagents for experimental and research purposes.

SEQUENCE LISTING

<160> NUMBER OF SEQ ID NOS: 5

<210> SEQ ID NO 1
<211> LENGTH: 85
<212> TYPE: DNA
<213> ORGANISM: Hepatitis delta virus
<220> FEATURE:
<223> OTHER INFORMATION: Modified hepatitis delta virus ribozyme cDNA

<400> SEQUENCE: 1
gggtcggcat ggcatctcca cctcctcgcg gtccgacctg ggcatccgaa ggaggacgcg    60
tccactcgga tggctaaggg agagc    85

<210> SEQ ID NO 2
<211> LENGTH: 55
<212> TYPE: DNA
<213> ORGANISM: Satellite tabacco ringspot virus
<220> FEATURE:
<223> OTHER INFORMATION: Modified satellite tabacco ringspot virus
      ribozyme cDNA

<400> SEQUENCE: 2
gtcaccggat gtgttttccg gtctgatgag tccgtgagga cg an inducible promoter which is $O_{LexA}$-46 located upstream of the cDNA of the RNA virus vector, wherein the virus vector cDNA is transcribed under the control of the inducible promoter; and a ribozyme sequence of satellite tobacco ringspot virus directly ligated to the 3' end of the RNA virus vector cDNA with no sequence ligated therebetween.

2. A process for producing a tobacco BY2 cell for protein production as set forth in claim 1, wherein the gene encoding the target protein replaces a viral coat protein gene.

3. A process for producing a tobacco BY2 cell for protein production as set forth in claim 1, wherein the transcription factor-expressing DNA and the protein-expressing DNA are transfected by an Agrobacterium method.

4. A plant culture tobacco BY2 cell for protein production, which is produced by the process for producing a tobacco BY2 cell for protein production as set forth in claim 1.

5. A protein producing process comprising, culturing the tobacco BY2 cell of claim 4 in the presence of estrogen.

* * * * *